United States Patent
Costantino

(10) Patent No.: US 10,668,142 B2
(45) Date of Patent: *Jun. 2, 2020

(54) INJECTABLE VACCINES AGAINST MULTIPLE MENINGOCOCCAL SEROGROUPS

(71) Applicant: GLAXOSMITHKLINE BIOLOGICALS, SA, Rixensart (BE)

(72) Inventor: Paolo Costantino, Siena (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/962,507

(22) Filed: Apr. 25, 2018

(65) Prior Publication Data

US 2018/0243395 A1    Aug. 30, 2018

Related U.S. Application Data

(62) Division of application No. 15/240,385, filed on Aug. 18, 2016, now Pat. No. 9,981,031, which is a division of application No. 10/543,455, filed as application No. PCT/IB2004/000651 on Jan. 30, 2004, now Pat. No. 10,272,147.

(30) Foreign Application Priority Data

Jan. 30, 2003 (GB) .................................. 0302217.5
Oct. 2, 2003 (GB) .................................. 0323101.6

(51) Int. Cl.

| A61K 39/095 | (2006.01) |
|---|---|
| A61K 9/00 | (2006.01) |
| C07K 14/22 | (2006.01) |
| A61K 39/08 | (2006.01) |
| A61K 39/116 | (2006.01) |
| A61K 39/05 | (2006.01) |
| A61K 39/385 | (2006.01) |
| A61K 39/00 | (2006.01) |
| A61K 39/102 | (2006.01) |
| A61K 39/09 | (2006.01) |
| A61K 39/29 | (2006.01) |
| A61K 39/02 | (2006.01) |
| A61K 39/12 | (2006.01) |

(52) U.S. Cl.
CPC .......... *A61K 39/095* (2013.01); *A61K 9/0019* (2013.01); *C07K 14/22* (2013.01); *A61K 39/0017* (2013.01); *A61K 39/0018* (2013.01); *A61K 39/05* (2013.01); *A61K 39/08* (2013.01); *A61K 39/092* (2013.01); *A61K 39/099* (2013.01); *A61K 39/102* (2013.01); *A61K 39/116* (2013.01); *A61K 39/12* (2013.01); *A61K 39/292* (2013.01); *A61K 39/385* (2013.01); *A61K 2039/54* (2013.01); *A61K 2039/545* (2013.01); *A61K 2039/55505* (2013.01); *A61K 2039/575* (2013.01); *A61K 2039/6037* (2013.01); *A61K 2039/62* (2013.01); *A61K 2039/627* (2013.01); *A61K 2039/70* (2013.01)

(58) Field of Classification Search
CPC .... A61K 39/095; A61K 9/092; A61K 39/102; A61K 39/12; A61K 39/13; A61K 39/29; A61K 39/292; A61K 39/39; A61K 2039/6037; A61K 2039/70; A61K 2039/55505; A61K 39/00; A61K 39/05; A61K 39/08; A61K 39/099; A61K 47/646; A61K 31/7028; A61K 39/0018; A61K 47/10; A61K 47/183; Y02A 50/466; A61P 31/00; B01D 15/3828; C07K 14/22; C07K 16/1217; C07K 14/005; C12N 2730/10122; C12N 2730/10134

See application file for complete search history.

(56) References Cited

U.S. PATENT DOCUMENTS

| 8,753,651 B2 * | 6/2014 | Costantino | ........... | A61K 39/095 424/250.1 |
|---|---|---|---|---|
| 8,889,152 B2 * | 11/2014 | Costantino | ........... | A61K 39/095 424/250.1 |
| 8,926,992 B2 * | 1/2015 | Del Guidice | ........ | A61K 39/095 424/241.1 |

FOREIGN PATENT DOCUMENTS

WO     WO 03/094834 A2 * 11/2003

* cited by examiner

*Primary Examiner* — Sarvamangala Devi
(74) *Attorney, Agent, or Firm* — Lisa Matovcik

(57) ABSTRACT

An injectable immunogenic composition comprising capsular saccharides from at least two of serogroups A, C, W135 and Y of *Neisseria meningitidis*, wherein said capsular saccharides are conjugated to carrier protein(s) and/or are oligosaccharides, and wherein (i) the composition comprises <50 μg meningococcal saccharide per dose, and/or (ii) the composition further comprises an antigen from one or more of: (a) serogroup B *N. meningitidis*; (b) *Haemophilus influenzae* type B; and/or (c) *Streptococcus pneumoniae*. Saccharide antigens in the compositions are generally conjugated to a carrier.

2 Claims, No Drawings
Specification includes a Sequence Listing.

INJECTABLE VACCINES AGAINST MULTIPLE MENINGOCOCCAL SEROGROUPS

CROSS REFERENCE TO RELATED APPLICATIONS

This application, filed Apr. 25, 2018, is a Divisional of U.S. patent application Ser. No. 15/240,385, filed Aug. 18, 2016, now U.S. Pat. No. 9,981,031, which is a Divisional of U.S. patent application Ser. No. 10/543,455, filed Nov. 6, 2006, now pending, which is the § 371 National Stage of International Patent Application No. PCT/162004/000651, filed Jan. 30, 2004, which claims foreign priority to United Kingdom Patent Application No. 0323101.6, filed Oct. 2, 2003, and United Kingdom Patent Application No. 0302217.5, filed Jan. 30, 2003, each of which is hereby incorporated by reference in its entirety.

SUBMISSION OF SEQUENCE LISTING AS ASCHII TEXT FILE

The content of the following submission on ASCII text file is incorporated herein by reference in its entirety: a computer readable form (CRF) of the Sequence Listing (file name: 303822006710SEQUST.TXT, date recorded: Aug. 17, 2016, size: 31 KB).

TECHNICAL FIELD

This invention is in the field of vaccines, particularly against bacterial meningitis.

BACKGROUND ART

*Neisseria meningitidis* is a Gram-negative human pathogen [1] which causes bacterial meningitis. It is closely related to *N. gonorrhoeae*, although one feature that clearly differentiates meningococcus is the presence of a polysaccharide capsule that is present in all pathogenic meningococci.

Based on the organism's capsular polysaccharide, twelve serogroups of *N. meningitidis* have been identified (A, B, C, H, I, K, L, 29E, W135, X, Y & Z). Serogroup A ('MenA') is most common cause of epidemic disease in sub-Saharan Africa. Serogroups B & C are responsible for the majority of cases in developed countries, with the remaining cases being caused by serogroups W135 & Y.

As well as being used for classification, the capsular polysaccharide has been used for vaccination. An injectable tetravalent vaccine of capsular polysaccharides from serogroups A, C, Y & W135 has been known for many years [2,3] and is licensed for human use. Although effective in adolescents and adults, it induces a poor immune response and short duration of protection and cannot be used in infants [e.g. 4]. The polysaccharides in this vaccine are unconjugated and are present at a 1:1:1:1 weight ratio [5]. Mencevax ACWY™ and Menomune™ both contain 50 µg of each purified polysaccharide once reconstituted from their lyophilised forms. The capsular saccharides of serogroups A, C, W135 & Y have also been combined in the form of conjugates [6-9] to give tetravalent vaccines e.g. the unadjuvanted Menactra™ product.

Conjugated serogroup C oligosaccharides have been approved for human use, including Menjugate™ [10,11], Meningitec™ and NeisVac-C™. The Menjugate™ and Meningitec™ products have oligosaccharide antigens conjugated to a $CRM_{197}$ carrier, whereas NeisVac-C™ uses the complete polysaccharide (de-O-acetylated) conjugated to a tetanus toxoid carrier.

There remains, however, a need for improvements in conjugate vaccines against serogroups A, W135 and Y, and in their manufacture. That need is addressed by the products, processes and uses disclosed in reference 7, but there remains scope for further modifications and improvements.

DISCLOSURE OF THE INVENTION

The invention provides an injectable immunogenic composition comprising capsular saccharides from at least two of serogroups A, C, W135 and Y of *N. meningitidis*, wherein said capsular saccharides are conjugated to carrier protein(s) and/or are oligosaccharides, and wherein the composition comprises ≤50 µg meningococcal saccharide per dose.

The invention also provides an injectable immunogenic composition comprising capsular saccharides from at least two of serogroups A, C, W135 and Y of *N. meningitidis*, wherein said capsular saccharides are conjugated to carrier protein(s) and/or are oligosaccharides, and wherein the composition further comprises an antigen from one or more of: (a) serogroup B *N. meningitidis*; (b) *Haemophilus influenzae* type B; and/or (c) *Streptococcus pneumoniae*.

Antigens included in sixteen preferred compositions of the invention are: (1) serogroups C, W135 & Y of *N. meningitidis*; (2) serogroups A, C, W135 & Y of *N. meningitidis*; (3) serogroups B, C, W135 & Y of *N. meningitidis*; (4) serogroups A, B, C, W135 & Y of *N. meningitidis*; (5) *H. influenzae* type B and serogroups C, W135 & Y of *N. meningitidis*; (6) *H. influenzae* type B and serogroups A, C, W135 & Y of *N. meningitidis*; (7) *H. influenzae* type B and serogroups B, C, W135 & Y of *N. meningitidis*; (8) *H. influenzae* type B and serogroups A, B, C, W135 & Y of *N. meningitidis*; (9) *S. pneumoniae* and serogroups C, W135 & Y of *N. meningitidis*; (10) *S. pneumoniae* and serogroups A, C, W135 & Y of *N. meningitidis*; (11) *S. pneumoniae* and serogroups B, C, W135 & Y of *N. meningitidis*; (12) *S. pneumoniae* and serogroups A, B, C, W135 & Y of *N. meningitidis*; (13) *H. influenzae* type B, *S. pneumoniae* and serogroups C, W135 & Y of *N. meningitidis*; (14) *H. influenzae* type B, *S. pneumoniae* and serogroups A, C, W135 & Y of *N. meningitidis*; (15) *H. influenzae* type B, *S. pneumoniae* and serogroups B, C, W135 & Y of *N. meningitidis*; (16) *H. influenzae* type B, *S. pneumoniae* and serogroups A, B, C, W135 & Y of *N. meningitidis*.

Saccharide antigens in the compositions of the invention are preferably conjugated to a carrier. Saccharide antigens in the compositions of the invention are preferably oligosaccharides. Saccharide antigens in the compositions of the invention are most preferably conjugated oligosaccharides.

Meningococcal Saccharide Mixtures

The compositions of the invention comprise capsular saccharides from at least two (i.e. 2, 3 or 4) of serogroups A, C, W135 and Y of *N. meningitidis*. Compositions of the invention preferably include *N. meningitidis* saccharides from at least serogroups C, W135 and Y (i.e. no MenA saccharide). It is preferred that the protective efficacy of individual saccharide antigens is not removed by combining them, although actual immunogenicity (e.g. ELISA titres) may be reduced.

Mixtures of saccharides from more than one serogroup of *N. meningitidis* are preferred e.g. compositions comprising saccharides from serogroups A+C, A+W135, A+Y, C+W135, C+Y, W135+Y, A+C+W135, A+C+Y, C+W135+Y, A+C+W135+Y, etc. Preferred compositions comprise saccharides from serogroups C and Y. Other preferred compositions comprise saccharides from serogroups C, W135 and Y. Compositions in which the capsular saccharides are from groups A and C only are not preferred (cf. refs. 10, 13 & 14).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher).

Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower).

A typical quantity of each meningococcal saccharide antigen per dose is between 1 µg and 20 µg e.g. about 1 µg, about 2.5 µg, about 4 µg, about 5 µg, or about 10 µg (expressed as saccharide).

Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Purification of Capsular Polysaccharides

Meningococcal capsular polysaccharides are typically prepared by a process comprising the steps of polysaccharide precipitation (e.g. using a cationic detergent), ethanol fractionation, cold phenol extraction (to remove protein) and ultracentrifugation (to remove LPS) [e.g. ref. 15].

A more preferred process [7], however, involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [16]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

As an alternative to purification, capsular saccharides of the present invention may be obtained by total or partial synthesis e.g. Hib synthesis is disclosed in ref. 17, and MenA synthesis in ref. 18.

The polysaccharide may be chemically modified. For instance, it may be modified to replace one or more hydroxyl groups with blocking groups. This is particularly useful for reducing hydrolysis for serogroup A [19] (see below). De-O-acetylation of saccharides can also be performed.

Serogroup B N. meningitidis

Some compositions of the invention include an antigen from serogroup B N. meningitidis. Unlike serogroups A, C, W135 and Y, the capsular saccharide of MenB is unsuitable for use as an immunogen in humans because of its similarity to self antigens. If a saccharide antigen is to be used for MenB, therefore, it is necessary to use a modified saccharide, such as one in which N-acetyl groups in the saccharide's sialic acid residues are replaced with N-acyl groups. Suitable N-acyl groups are $C_1$ to $C_8$ acyl groups, such as N-propionyl [20]. Rather than use a saccharide antigen, however, it is preferred to use a polypeptide antigen.

Thus the composition may include one or more polypeptide antigens which induce(s) an immune response that protects against MenB infection and/or that is bactericidal against MenB. More generally, the composition can preferably, after administration to a subject, induce an antibody response in that subject that is bactericidal against two or more (e.g. 2 or 3) of hypervirulent lineages A4, ET-5 and lineage 3 of N. meningitidis serogroup B.

The genome sequence of strain MC58 of MenB has been published [21] and suitable antigens can be selected from the encoded polypeptides [22]. Preferred antigens are disclosed in references 22 to 32. Rather than consisting of a single antigen, it is preferred that the composition of the invention comprises a mixture of 10 or fewer (e.g. 9, 8, 7, 6, 5, 4, 3, 2) purified antigens, and it is particularly preferred that the composition should not include complex or undefined mixtures of antigens e.g. it is preferred not to include outer membrane vesicles (OMVs) in the composition.

Preferred compositions include one or more of the following five antigens [32]: (1) a 'NadA' protein, preferably in oligomeric form (e.g. in trimeric form); (2) a '741' protein; (3) a '936' protein; (4) a '953' protein; and (5) a '287' protein.

Preferred MenB antigens comprise an amino acid sequence found in one of strains are 2996, MC58, 95N477, and 394/98. Protein 287 is preferably from strain 2996 or, more preferably, from strain 394/98. Protein 741 is preferably from serogroup B strains MC58, 2996, 394/98, or 95N477, or from serogroup C strain 90/18311. Strain MC58 is more preferred. Proteins 936, 953 and NadA are preferably from strain 2996. Where a composition includes a particular protein antigen (e.g. 741 or 287), the composition can include that antigen in more than one variant form e.g. the same protein, but from more than one strain. These proteins may be included as tandem or separate proteins.

'NadA' (Neisserial adhesin A) from MenB is disclosed as protein '961' in reference 25 (SEQ IDs 2943 & 2944) and as 'NMB1994' in reference 21 (see also GenBank accession numbers: 11352904 & 7227256). A detailed study of the protein can be found in reference 33. When used according to the present invention, NadA may take various forms. Preferred forms of NadA are truncation or deletion variants, such as those disclosed in references 29 to 31. In particular, NadA without its C-terminal membrane anchor is preferred (e.g. deletion of residues 351-405 for the 2996 strain, to give SEQ ID NO:1 herein), which is sometimes distinguished herein by the use of a 'C' superscript e.g. $NadA^{(C)}$. Expression of NadA without its membrane anchor domain in E. coli results in secretion of the protein into the culture supernatant with concomitant removal of its 23mer leader peptide (e.g. to leave a 327mer for strain 2996 [SEQ ID NO:2 herein]). Polypeptides without their leader peptides are sometimes distinguished herein by the use of a 'NL' superscript e.g.

NadA$^{(NL)}$ or NadA$^{(C)(NL)}$). Preferred NadA polypeptides have an amino acid sequence which: (a) has 50% or more identity (e.g. 60%, 70%, 80%, 90%, 95%, 99% or more) to SEQ ID NO:2; and/or (b) comprises a fragment of at least n consecutive amino acids of SEQ ID NO:1, wherein n is 7 or more (eg. 8, 10, 12, 14, 16, 18, 20, 25, 30, 35, 40, 50, 60, 70, 80, 90, 100, 150, 200, 250 or more). Preferred fragments for (b) lack one or more amino acids (e.g. 1, 2, 3, 4, 5, 6, 7, 8, 9, 10, 15, 20, 25 or more) from the C-terminus and/or the N-terminus of SEQ ID NO:1 (e.g. NadA$^{(C)}$, NadA$^{(NL)}$, NadA$^{(C)(NL)}$). Other preferred fragments comprise an epitope from SEQ ID 1, and a particularly preferred fragment of SEQ ID 1 is SEQ ID 2. These various sequences includes NadA variants (e.g. allelic variants, homologs, orthologs, paralogs, mutants, etc.). Various NadA sequences are shown in FIG. 9 of reference 34.

'741' protein from MenB is disclosed in reference 25 (SEQ IDs 2535 & 2536) and as 'NMB1870' in reference 21 (see also GenBank accession number GI:7227128). The corresponding protein in serogroup A [35] has GenBank accession number 7379322. 741 is naturally a lipoprotein. When used according to the present invention, 741 protein may take various forms. Preferred forms of 741 are truncation or deletion variants, such as those disclosed in references 29 to 31. In particular, the N-terminus of 741 may be deleted up to and including its poly-glycine sequence (i.e. deletion of residues 1 to 72 for strain MC58 [SEQ ID NO:3 herein]), which is sometimes distinguished herein by the use of a 'ΔG' prefix. This deletion can enhance expression. The deletion also removes 741's lipidation site. Preferred 741 sequences have an amino acid sequence which: (a) has 50% or more identity (e.g. 60%, 70%, 80%, 90%, 95%, 99% or more) to SEQ ID NO:3; and/or (b) comprises a fragment of at least n consecutive amino acids from SEQ ID NO:3, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 741. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:3. These sequences include 741 variants (e.g. allelic variants, homologs, orthologs, paralogs, mutants, etc.). Various 741 sequences can be found in SEQ IDs 1 to 22 of reference 31, in SEQ IDs 1 to 23 of reference 36, and in SEQ IDs 1-299 of reference 37.

Protein 741 is an extremely effective antigen for eliciting anti-meningococcal antibody responses, and it is expressed across all meningococcal serogroups. Phylogenetic analysis shows that the protein splits into two groups, and that one of these splits again to give three variants in total [38], and while serum raised against a given variant is bactericidal within the same variant group, it is not active against strains which express one of the other two variants i.e. there is intra-variant cross-protection, but not inter-variant cross-protection [36,38]. For maximum cross-strain efficacy, therefore, it is preferred that a composition should include more than one variant of protein 741. An exemplary sequence from each variant is given in SEQ ID NOs: 10, 11 and 12 herein, starting with a N-terminal cysteine residue to which lipid will be covalently attached in the native lipoprotein form. It is therefore preferred that the composition should include at least two of: (1) a first protein, comprising an amino acid sequence having at least a % sequence identity to SEQ ID NO:10 and/or comprising an amino acid sequence consisting of a fragment of at least x contiguous amino acids from SEQ ID NO:10; (2) a second protein, comprising an amino acid sequence having at least b % sequence identity to SEQ ID NO:11 and/or comprising an amino acid sequence consisting of a fragment of at least y contiguous amino acids from SEQ ID NO:11; and (3) a third protein, comprising an amino acid sequence having at least c % sequence identity to SEQ ID NO:12 and/or comprising an amino acid sequence consisting of a fragment of at least z contiguous amino acids from SEQ ID NO:12. The value of a is at least 85 e.g. 86, 87, 88, 89, 90, 91, 92, 93, 94, 95, 96, 97, 98, 99, 99.5, or more. The value of b is at least 85 e.g. 86, 87, 88, 89, 90, 91, 92, 93, 94, 95, 96, 97, 98, 99, 99.5, or more. The value of c is at least 85 e.g. 86, 87, 88, 89, 90, 91, 92, 93, 94, 95, 96, 97, 98, 99, 99.5, or more. The values of a, b and c are not intrinsically related to each other. The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other. It is preferred that any given 741 amino acid sequence will not fall into more than one of categories (1), (2) and (3). Any given 741 sequence will thus fall into only one of categories (1), (2) and (3). It is thus preferred that: protein (1) has less than i % sequence identity to protein (2); protein (1) has less than j % sequence identity to protein (3); and protein (2) has less than k % sequence identity to protein (3). The value of i is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most a. The value of j is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most b. The value of k is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most c. The values of i, j and k are not intrinsically related to each other.

'936' protein from serogroup B is disclosed in reference 25 (SEQ IDs 2883 & 2884) and as 'NMB2091' in reference 21 (see also GenBank accession number GI:7227353). The corresponding gene in serogroup A [35] has GenBank accession number 7379093. When used according to the present invention, 936 protein may take various forms. Preferred forms of 936 are truncation or deletion variants, such as those disclosed in references 29 to 31. In particular, the N-terminus leader peptide of 936 may be deleted (e.g. deletion of residues 1 to 23 for strain MC58, to give 936$^{(NL)}$ [SEQ ID NO:4 herein]). Preferred 936 sequences have an amino acid sequence which: (a) has 50% or more identity (e.g. 60%, 70%, 80%, 90%, 95%, 99% or more) to SEQ ID NO:4; and/or (b) comprises a fragment of at least n consecutive amino acids from SEQ ID NO:4, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 936. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:4. These sequences include 936 variants (e.g. allelic variants, homologs, orthologs, paralogs, mutants, etc.).

'953' protein from serogroup B is disclosed in reference 25 (SEQ IDs 2917 & 2918) and as 'NMB1030' in reference 21 (see also GenBank accession number GI:7226269). The corresponding protein in serogroup A [35] has GenBank accession number 7380108. When used according to the present invention, 953 protein may take various forms. Preferred forms of 953 are truncation or deletion variants, such as those disclosed in references 29 to 31. In particular, the N-terminus leader peptide of 953 may be deleted (e.g. deletion of residues 1 to 19 for strain MC58, to give 953$^{(\Delta L)}$ [SEQ ID NO:5 herein]. Preferred 953 sequences have an amino acid sequence which: (a) has 50% or more identity (e.g. 60%, 70%, 80%, 90%, 95%, 99% or more) to SEQ ID NO:5; and/or (b) comprises a fragment of at least n consecutive amino acids from SEQ ID NO:5, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 953. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:5. These sequences include 936 variants (e.g. allelic variants, homologs, orthologs, paralogs, mutants, etc.). Allelic forms of 953 can be seen in FIG. 19 of reference 28.

'287' protein from serogroup B is disclosed in reference 25 (SEQ IDs 3103 & 3104), as 'NMB2132' in reference 21, and as 'GNA2132' in reference 22 (see also GenBank accession number GI:7227388). The corresponding protein in serogroup A [35] has GenBank accession number 7379057. When used according to the present invention, 287 protein may take various forms. Preferred forms of 287 are truncation or deletion variants, such as those disclosed in references 29 to 31. In particular, the N-terminus of 287 may be deleted up to and including its poly-glycine sequence (e.g. deletion of residues 1 to 24 for strain MC58, to give ΔG287 [SEQ ID NO:6 herein]. This deletion can enhance expression. Preferred 287 sequences have an amino acid sequence which: (a) has 50% or more identity (e.g. 60%, 70%, 80%, 90%, 95%, 99% or more) to SEQ ID NO:6; and/or (b) comprises a fragment of at least n consecutive amino acids from SEQ ID NO:6, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 287. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:6. These sequences include 287 variants (e.g. allelic variants, homologs, orthologs, paralogs, mutants, etc.). Allelic forms of 287 can be seen in FIGS. 5 and 15 of reference 28, and in example 13 and FIG. 21 of reference 25 (SEQ IDs 3179 to 3184).

The five basic MenB antigens (NadA, 741, 953, 936 & 287) may be present in the composition as five separate proteins, but it is preferred that at least two of the antigens are expressed as a single polypeptide chain (a 'hybrid' protein [refs. 29 to 31]) i.e. such that the five antigens form fewer than five polypeptides. Hybrid proteins offer two principal advantages: first, a protein that may be unstable or poorly expressed on its own can be assisted by adding a suitable hybrid partner that overcomes the problem; second, commercial manufacture is simplified as only one expression and purification need be employed in order to produce two separately-useful proteins. A hybrid protein included in a composition of the invention may comprise two or more (i.e. 2, 3, 4 or 5) of the five basic antigens. Hybrids consisting of two of the five antigens are preferred.

Within the combination of five basic antigens, an antigen may be present in more than one hybrid protein and/or as a non-hybrid protein. It is preferred, however, that an antigen is present either as a hybrid or as a non-hybrid, but not as both, although it may be useful to include protein 741 both as a hybrid and a non-hybrid (preferably lipoprotein) antigen, particularly where more than one variant of 741 is used.

Hybrid proteins can be represented by the formula NH$_2$-A-[—X-L-]$_n$—B—COOH, wherein: X is an amino acid sequence of one of the five basic antigens; L is an optional linker amino acid sequence; A is an optional N-terminal amino acid sequence; B is an optional C-terminal amino acid sequence; and n is 2, 3, 4 or 5.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of [—X-L-], linker amino acid sequence -L- may be present or absent. For instance, when n=2 the hybrid may be NH$_2$—$X_1$-$L_1$-$X_2$-$L_2$-COOH, NH$_2$—$X_1$—$X_2$—COOH, NH$_2$—$X_1$-$L_1$-$X_2$—COOH, NH$_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID 9), with the Gly-Ser dipeptide being formed from a BamHI restriction site, thus aiding cloning and manipulation, and the (Gly)$_4$ tetrapeptide being a typical poly-glycine linker. If $X_{n+1}$ is a ΔG protein and $L_n$ is a glycine linker, this may be equivalent to $X_{n+1}$ not being a ΔG protein and $L_n$ being absent.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more), or sequences which enhance protein stability. Other suitable C-terminal amino acid sequences will be apparent to those skilled in the art.

Most preferably, n is 2. Two-antigen hybrids for use in the invention comprise: NadA & 741; NadA & 936; NadA & 953; NadA & 287; 741 & 936; 741 & 953; 741 & 287; 936 & 953; 936 & 287; 953 & 287. Two preferred proteins are: $X_1$ is a 936 and $X_2$ is a 741; $X_1$ is a 287 and $X_2$ is a 953.

Two particularly preferred hybrid proteins of the invention are as follows:

| n | A | X₁ | L₁ | X₂ | L₂B | SEQ ID NO: |
|---|----|------|-------------------|-----------|-----|-----|
| 2 | MA | ΔG287 | GSGGGG (SEQ ID NO 9) | 953 (NL) | — — | 7 |
| 2 | M  | 936 (NL) | GSGGGG (SEQ ID NO 9) | ΔG741 | — — | 8 |

These two proteins may be used in combination with NadA (particularly with SEQ ID NO:2). Thus a preferred composition of MenB antigens for use with the invention thus includes a first polypeptide comprising amino acid sequence SEQ ID NO:2, a second polypeptide comprising amino acid sequence SEQ ID NO:7 and a third polypeptide comprising amino acid sequence SEQ ID NO:8. This is a preferred group of MenB antigens for use with the invention.

As mentioned above, compositions of the invention that include MenB antigens can preferably induce a serum bactericidal antibody response that is effective against two or three of MenB hypervirulent lineages A4, ET-5 and lineage 3. They may additionally induce bactericidal antibody responses against one or more of hypervirulent lineages subgroup I, subgroup III, subgroup Iv-1 or ET-37 complex, and against other lineages e.g. hyperinvasive lineages. These antibody responses are conveniently measured in mice and are a standard indicator of vaccine efficacy [e.g. see end-note 14 of reference 22]. Serum bactericidal activity (SBA) measures bacterial killing mediated by complement, and can be assayed using human or baby rabbit complement. WHO standards require a vaccine to induce at least a 4-fold rise in SBA in more than 90% of recipients.

The composition need not induce bactericidal antibodies against each and every MenB strain within these hypervirulent lineages; rather, for any given group of four of more strains of serogroup B meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1/1024, as described in reference 22. Preferred compositions can induce bactericidal responses against the following strains of serogroup B meningococcus: (i) from cluster A4, strain 961-5945 (B:2b:P1.21,16) and/or strain G2136 (B:-); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:-). More preferred compositions can induce bactericidal responses against strains 961-5945, 44/76 and 394/98. Strains 961-5945 and G2136 are both *Neisseria* MLST reference strains [ids 638 & 1002 in ref. 39]. Strain MC58 is widely available (e.g. ATCC BAA-335) and was the strain sequenced in reference 21. Strain 44/76 has been widely used and characterised (e.g. ref. 40) and is one of the *Neisseria* MLST reference strains [id 237 in ref. 39; row 32 of Table 2 in ref. 41]. Strain 394/98 was originally isolated in New Zealand in 1998, and there have been several published studies using this strain (e.g. refs. 42 & 43). Strain BZ198 is another MLST reference strain [id 409 in ref. 39; row 41 of Table 2 in ref. 41]. The composition may additionally induce a bactericidal response against serogroup W135 strain LNP17592 (W135:2a:P1.5,2), from ET-37 complex. This is a Haji strain isolated in France in 2000.

Other MenB polypeptide antigens which may be included in compositions of the invention include those comprising one of the following amino acid sequences: SEQ ID NO:650 from ref. 23; SEQ ID NO:878 from ref. 23; SEQ ID NO:884 from ref. 23; SEQ ID NO:4 from ref. 24; SEQ ID NO:598 from ref. 25; SEQ ID NO:818 from ref. 25; SEQ ID NO:864 from ref. 25; SEQ ID NO:866 from ref. 25; SEQ ID NO:1196 from ref. 25; SEQ ID NO:1272 from ref. 25; SEQ ID NO:1274 from ref. 25; SEQ ID NO:1640 from ref. 25; SEQ ID NO:1788 from ref. 25; SEQ ID NO:2288 from ref. 25; SEQ ID NO:2466 from ref. 25; SEQ ID NO:2554 from ref. 25; SEQ ID NO:2576 from ref. 25; SEQ ID NO:2606 from ref. 25; SEQ ID NO:2608 from ref. 25; SEQ ID NO:2616 from ref. 25; SEQ ID NO:2668 from ref. 25; SEQ ID NO:2780 from ref. 25; SEQ ID NO:2932 from ref. 25; SEQ ID NO:2958 from ref. 25; SEQ ID NO:2970 from ref. 25; SEQ ID NO:2988 from ref. 25, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6) of these polypeptides may be included.

*Haemophilus influenzae* Type B (Hib)

Where the composition includes a *H. influenzae* type B antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented [e.g. references 44 to 52 etc.]. The invention may use any suitable Hib conjugate. Suitable carrier proteins are described below, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [53, 54]. Tetanus toxoid is also a preferred carrier.

Administration of the Hib antigen preferably results in an anti-PRP antibody concentration of ≥0.15 µg/ml, and more preferably ≥1 µg/ml.

Compositions of the invention may comprise more than one Hib antigen.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [55] or it may be non-adsorbed [12]. Prevention of adsorption can be achieved by selecting the correct pH during antigen/adjuvant mixing, an adjuvant with an appropriate point of zero charge, and an appropriate order of mixing for the various different antigens in a composition [56].

Hib antigens may be lyophilised e.g. together with meningococcal antigens.

Streptococcus pneumoniae

Where the composition includes a *S. pneumoniae* antigen, it will typically be a capsular saccharide antigen which is preferably conjugated to a carrier protein [e.g. refs. 57 to 59]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [60]. For example, PrevNar™ [61] contains antigens from seven serotypes (4, 6B, 9V, 14, 18C, 19F, and 23F) with each saccharide individually conjugated to $CRM_{197}$ by reductive amination, with 2 μg of each saccharide per 0.5 ml dose (4 μg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [62,63] and can be subjected to reverse vaccinology [64-67] to identify suitable polypeptide antigens [68,69]. For example, the composition may include one or more of the following antigens: PhtA, PhtD, PhtB, PhtE, SpsA, LytB, LytC, LytA, Sp125, Sp101, Sp128, Sp130 and Sp130, as defined in reference 70. The composition may include more than one (e.g. 2, 3, 4, 5, 6, 7, 8, 9 10, 11, 12, 13 or 14) of these antigens.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [70].

Pneumococcal antigens may be lyophilised e.g. together with meningococcal and/or Hib antigens.

Modified Serogroup a *N. meningitidis* Saccharides

Where a composition of the invention includes a MenA saccharide antigen, the antigen is preferably a modified saccharide in which one or more of the hydroxyl groups on the native saccharide has/have been replaced by a blocking group [19]. This modification improves resistance to hydrolysis, and means that the serogroup A antigen can be stored and used in a liquid formulation rather than requiring lyophilisation.

The number of monosaccharide units having blocking groups can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on a monosaccharide unit may be 1 or 2. The blocking group will generally be at the 4 position and/or 3-position of the monosaccharide units.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups (—$NH_2$ or —NH-E, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}$ alkyl), CN, $CF_3$, $CCl_3$, etc. Preferred blocking groups are electron-withdrawing groups.

Preferred blocking groups are of the formula: —O—X—Y or —$OR^3$ wherein: X is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, Cl, Br, $CO_2H$, $CO_2(C_{1-6}$ alkyl), CN, $CF_3$ or $CCl_3$; or Y is $NR^1R^2$; $R^1$ and $R^2$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^1$ and $R^2$ may be joined to form a $C_{3-12}$ saturated heterocyclic group; $R^3$ is $C_{1-12}$ alkyl or $C_{3-12}$ cycloalkyl, each of which may optionally be substituted with 1, 2 or 3 groups independently selected from F, Cl, Br, $CO_2(C_{1-6}$ alkyl), CN, $CF_3$ or $CCl_3$; or $R^3$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^3$ is $C_{1-12}$ alkyl or $C_{3-12}$ cycloalkyl, it is typically substituted with 1, 2 or 3 groups as defined above. When $R^1$ and $R^2$ are joined to form a $C_{3-12}$ saturated heterocyclic group, it is meant that $R^1$ and $R^2$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR^3$ can be prepared from —OH groups by standard derivatizing procedures, such as reaction of the hydroxyl group with an acyl halide, alkyl halide, sulfonyl halide, etc. Hence, the oxygen atom in —O—X—Y is preferably the oxygen atom of the hydroxyl group, while the -X-Y group in —O—X—Y preferably replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

More preferably, the blocking group is —OC(O)CF3 [71], or a carbamate group —OC(O)$NR^1R^2$, where $R^1$ and $R^2$ are independently selected from $C_{1-6}$ alkyl. More preferably, $R^1$ and $R^2$ are both methyl i.e. the blocking group is —OC(O)$NMe_2$. Carbamate blocking groups have a stabilizing effect on the glycosidic bond and may be prepared under mild conditions.

Preferred modified MenA saccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is preferably 50 or more. The absent —OH groups are preferably blocking groups as defined above.

Other preferred modified MenA saccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are preferably blocking groups as defined above.

Suitable modified MenA saccharides for use with the invention have the formula:

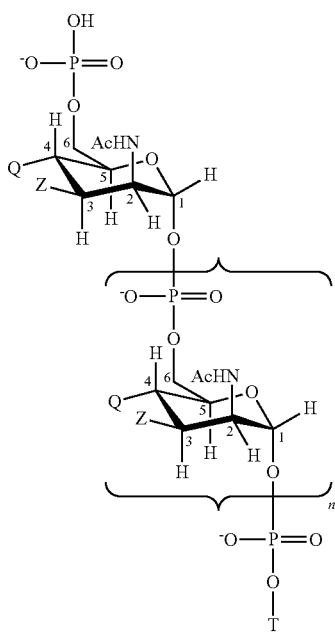

wherein n is an integer from 1 to 100 (preferably an integer from 15 to 25);

T is of the formula (A) or (B):

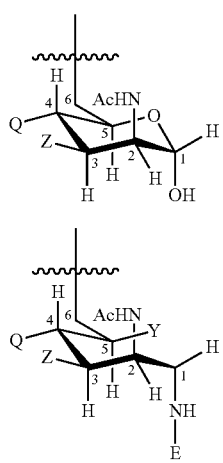

each Z group is independently selected from OH or a blocking group as defined above; and each Q group is independently selected from OH or a blocking group as defined above;

Y is selected from OH or a blocking group as defined above;

E is H or a nitrogen protecting group;

and wherein more than about 7% (e.g. 8%, 9%, 10% or more) of the Q groups are blocking groups.

Each of the n+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Preferably, about 70% of the Z groups are OAc, with the remainder of the Z groups being OH or blocking groups as defined above. At least about 7% of Q groups are blocking groups. Preferably, at least 10%, 20%, 30%, 40%, 50%, 60%, 70%, 80%, 90% or even 100% of the Q groups are blocking groups.

Preferred compositions of the invention can be stored for 28 days at 37° C. and, after that period, less than f % of the initial total amount of conjugated MenA saccharide will be unconjugated, where f is 20, 19, 18, 17, 16, 15, 14, 13, 12, 11, 10, 9, 8, 7, 6, 5 or lower.

Oligosaccharides

Capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [72].

Preferred MenC saccharide antigens are disclosed in reference 10, as used in Menjugate™.

If hydrolysis is performed, the hydrolysate will generally be sized in order to remove short-length oligosaccharides [73]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines [e.g. ref. 74] and is a well known technique [e.g. reviewed in refs. 44 to 52, etc.].

Preferred carrier proteins are bacterial toxins or toxoids, such as diphtheria toxoid or tetanus toxoid. The $CRM_{197}$ diphtheria toxoid [75-77] is particularly preferred. Other suitable carrier proteins include the N. meningitidis outer membrane protein [78], synthetic peptides [79,80], heat shock proteins [81,82], pertussis proteins [83, 84], cytokines [85], lymphokines [85], hormones [85], growth factors [85], artificial proteins comprising multiple human $CD4^+$ T cell epitopes from various pathogen-derived antigens [86], protein D from H. influenzae [87,88], pneumococcal surface protein PspA [89], iron-uptake proteins [90], toxin A or B from *C.difficile* [91], etc. Preferred carriers are diphtheria toxoid, tetanus toxoid, *H. influenzae* protein D, and $CRM_{197}$.

Within a composition of the invention, it is possible to use more than one carrier protein e.g. to reduce the risk of carrier suppression. Thus different carrier proteins can be used for different serogroups e.g. serogroup A saccharides might be conjugated to $CRM_{197}$ while serogroup C saccharides might be conjugated to tetanus toxoid. It is also possible to use more than one carrier protein for a particular saccharide antigen e.g. serogroup A saccharides might be in two groups, with some conjugated to $CRM_{197}$ and others conjugated to tetanus toxoid. In general, however, it is preferred to use the same carrier protein for all saccharides.

A single carrier protein might carry more than one saccharide antigen [92]. For example, a single carrier protein might have conjugated to it saccharides from serogroups A and C. To achieve this goal, saccharides can be mixed prior to the conjugation reaction. In general, however, it is preferred to have separate conjugates for each serogroup.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5 are more preferred. Excess carrier protein may be preferred for MenA and MenC.

Conjugates may be used in conjunction with free carrier protein [93]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [94,95,etc.]). Other suitable techniques use carbodiimides, hydrazides, active esters, norborane, p-nitrobenzoic acid, N-hydroxysuccinimide, S—NHS, EDC, TSTU; see also the introduction to reference 50).

Linkages via a linker group may be made using any known procedure, for example, the procedures described in references 96 and 97. One type of linkage involves reductive amination of the polysaccharide, coupling the resulting amino group with one end of an adipic acid linker group, and then coupling a protein to the other end of the adipic acid linker group [48, 98, 99]. Other linkers include B-propionamido [100], nitrophenyl-ethylamine [101], haloacyl halides [102], glycosidic linkages [103], 6-aminocaproic acid [104], ADH [105], $C_4$ to $C_{12}$ moieties [106] etc. As an alternative to using a linker, direct linkage can be used. Direct linkages to the protein may comprise oxidation of the polysaccharide followed by reductive amination with the protein, as described in, for example, references 107 and 108.

A process involving the introduction of amino groups into the saccharide (e.g. by replacing terminal =O groups with $—NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

After conjugation, free and conjugated saccharides can be separated. There are many suitable methods, including hydrophobic chromatography, tangential ultrafiltration, diafiltration etc. [see also refs. 109 & 110, etc.].

Where the composition of the invention includes a conjugated oligosaccharide, it is preferred that oligosaccharide preparation precedes conjugation.

Preparation of Compositions of the Invention

Compositions of the invention comprise capsular saccharides from at least two of serogroups A, C, W135 and Y of *N. meningitidis*. The saccharides are preferably prepared separately (including any fragmentation, conjugation, etc.) and then admixed to give a composition of the invention.

Where the composition comprises capsular saccharide from serogroup A, however, it is preferred that the serogroup A saccharide is not combined with the other saccharide(s) until shortly before use, in order to minimise the potential for hydrolysis. This can conveniently be achieved by having the serogroup A component (typically together with appropriate excipients) in lyophilised form and the other serogroup component(s) in liquid form (also with appropriate excipients), with the liquid components being used to reconstitute the lyophilised MenA component when ready for use. Where an aluminium salt adjuvant is used, it is preferred to include the adjuvant in the vial containing the with the liquid vaccine, and to lyophilise the MenA component without adjuvant.

A composition of the invention may thus be prepared from a kit comprising: (a) capsular saccharide from *N. meningitidis* serogroup A, in lyophilised form; and (b) capsular saccharide(s) from one or more (e.g. 1, 2, 3) of *N. meningitidis* serogroups C, W135 and Y, in liquid form. The invention also provides a method for preparing a composition of the invention, comprising mixing a lyophilised capsular saccharide from *N. meningitidis* serogroup A with capsular saccharide(s) from one or more (e.g. 1, 2, 3) of *N. meningitidis* serogroups C, W135 and Y, wherein said one or more saccharides are in liquid form.

The invention also provides a composition of the invention, comprising capsular saccharide(s) from *N. meningitidis* serogroups C, W135 and Y, wherein saccharides are in liquid form. This composition may be packaged with a lyophilised serogroup A saccharide antigen, for reconstitution, or it may be used as a composition on its own e.g. where immunisation against serogroup A is not desired.

The invention also provides a kit comprising: (a) a first container containing capsular saccharides from two or more of *N. meningitidis* serogroups C, W135 and Y, all in lyophilised form; and (b) a second container containing, in liquid form, (i) capsular saccharides from none or one of *N. meningitidis* serogroups C, W135 and Y, and optionally (ii) further antigens (see below) that do not include meningococcal capsular saccharides, wherein, reconstitution of the contents of container (a) by the contents of container (b) provides a composition of the invention.

Presentation of Compositions of the Invention

Compositions of the invention may be presented and packaged in various ways.

The compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where serogroup A saccharide is presented in lyophilised form) and is presented as a kit, the kit may comprise two vials, or it may comprise one ready-filled syringe and one vial, with the contents of the syringe being used to reactivate the contents of the vial prior to injection.

Within each dose, the amount of an individual saccharide antigen will generally be between 1-50 µg (measured as mass of saccharide), with about 2.5 µg, 5 µg or 10 µg of each being preferred. With A:C:W135:Y weight ratios of 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1, therefore, the amount represented by the FIG. 1 is preferably about 2.5 µg, 5 µg or 10 µg. For a 1:1:1:1 ratio A:C:W:Y composition and a 10 µg per saccharide, therefore, 40 µg saccharide is administered per dose. Preferred compositions have about the following µg saccharide per dose:

| A | 10 | 0 | 0 | 0 | 10 | 5 | 2.5 |
|---|----|----|----|-----|----|---|-----|
| C | 10 | 10 | 5 | 2.5 | 5 | 5 | 2.5 |
| W135 | 10 | 10 | 5 | 2.5 | 5 | 5 | 2.5 |
| Y | 10 | 10 | 5 | 2.5 | 5 | 5 | 2.5 |

Preferred compositions of the invention comprise less than 50 µg meningococcal saccharide per dose. Other preferred compositions comprise ≤40 µg meningococcal saccharide per dose. Other preferred compositions comprise ≤30 µg meningococcal saccharide per dose. Other preferred compositions comprise ≤25 µg meningococcal saccharide per dose. Other preferred compositions comprise ≤20 µg meningococcal saccharide per dose. Other preferred compositions comprise ≤10 µg meningococcal saccharide per dose but, ideally, compositions of the invention comprise at least 10 µg meningococcal saccharide per dose.

Compositions of the invention are preferably sterile. They are preferably pyrogen-free. They are preferably buffered e.g. at between pH 6 and pH 8, generally around pH 7. Where a composition comprises an aluminium hydroxide salt, it is preferred to use a histidine buffer [111]. Compositions of the invention may be isotonic with respect to humans.

Adjuvants

The compositions will generally include one or more adjuvants. The adjuvant(s) may be added to saccharides before and/or after they are admixed to form a composition of the invention, but it is preferred to combine adjuvant with a saccharide antigen prior to admixing of different saccharides.

However, it is not necessary that each saccharide must be adjuvanted prior to such admixing. Excess adjuvant can be included in one saccharide preparation such that, when further unadjuvanted saccharide antigen(s) is/are added, the excess is diluted to a desired final concentration. In one particular embodiment, where the composition of the invention is prepared from a lyophilised antigen (e.g. a lyophilised serogroup A component) it may be preferred not to include an adjuvant in the lyophilised material.

Preferred adjuvants for inclusion in compositions of the invention are aluminium salts (alum), such as aluminium hydroxides (including oxyhydroxides), aluminium phosphates (including hydroxyphosphates), aluminium sulfate, etc [Chapters 8 & 9 in ref. 112]. Aluminium hydroxyphosphate is particularly preferred, particularly in compositions which include a H. influenzae saccharide antigen, and a typical adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where there is more than one conjugate in a composition, not all conjugates need to be adsorbed. The Menjugate™ and NeisVac™ MenC conjugates use a hydroxide adjuvant, whereas Meningitec™ uses a phosphate.

Calcium phosphate is another preferred adjuvant.

Other adjuvants which may be used in addition to or in place of aluminium salts include:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 112], or mixtures of different mineral compounds, with the compounds taking any suitable form (e.g. gel, crystalline, amorphous, etc.), and with adsorption being preferred. The mineral containing compositions may also be formulated as a particle of metal salt [113].

B. Oil Emulsions

Oil emulsion compositions suitable for use as adjuvants in the invention include squalene-water emulsions, such as MF59™ [Chapter 10 of ref. 112; see also ref. 114] (5% Squalene, 0.5% TWEEN80™ and 0.5% SPAN 85™, formulated into submicron particles using a microfluidizer). Complete Freund's adjuvant (CFA) and incomplete Freund's adjuvant (IFA) may also be used.

C. Saponin Formulations [Chapter 22 of Ref 112]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the Quillaia saponaria Molina tree have been widely studied as adjuvants. Saponin can also be commercially obtained from Smilax ornata (sarsaprilla), Gypsophilla paniculata (brides veil), and Saponaria officianalis (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 114. Saponin formulations may also comprise a sterol, such as cholesterol [115].

Combinations of saponins and cholesterols can be used to form unique particles called immunostimulating complexes (ISCOMs) [chapter 23 of ref. 112]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 115-117. Optionally, the ISCOMS may be devoid of additional detergent [118].

A review of the development of saponin based adjuvants can be found in refs. 119 & 120.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein p1). VLPs are discussed further in refs. 121-126. Virosomes are discussed further in, for example, ref. 127

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 128. Such "small particles" of 3dMPL are small enough to be sterile filtered through a 0.22 µm membrane [128]. Other non-toxic LPS derivatives include monophosphoryl lipid A mimics, such as aminoalkyl glucosaminide phosphate derivatives e.g. RC-529 [129,130].

Lipid A derivatives include derivatives of lipid A from *Escherichia coli* such as OM-174. OM-174 is described for example in refs. 131 & 132.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 133, 134 and 135 disclose possible analog substitutions e.g. replacement of guanosine with 2'-deoxy-7-deazaguanosine. The adjuvant effect of CpG oligonucleotides is further discussed in refs. 136-141.

The CpG sequence may be directed to TLR9, such as the motif GTCGTT or TTCGTT [142]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 143-145. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 142 & 146-148.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 149 and as parenteral adjuvants in ref. 150. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 151-158. Numerical reference for amino acid substitutions is preferably based on the alignments of the A and B subunits of ADP-ribosylating toxins set forth in ref. 159, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [160], etc.) [161], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [162] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [163].

H. Microparticles Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 112)

Examples of liposome formulations suitable for use as adjuvants are described in refs. 164-166.

J. Polyoxyethylene Ether and Polyoxyethylene Ester Formulations

Adjuvants suitable for use in the invention include polyoxyethylene ethers and polyoxyethylene esters [167]. Such formulations further include polyoxyethylene sorbitan ester surfactants in combination with an octoxynol [168] as well as polyoxyethylene alkyl ethers or ester surfactants in combination with at least one additional non-ionic surfactant such as an octoxynol [169]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 170 and 171.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 172 and 173.

The invention may also comprise combinations one or more of the adjuvants identified above. For example, the following adjuvant compositions may be used in the invention: (1) a saponin and an oil-in-water emulsion [175]; (2) a saponin (e.g. QS21)+a non-toxic LPS derivative (e.g. 3dMPL) [176]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [177]; (5) combinations of 3dMPL with, for example, QS21 and/or oil-in-water emulsions [178]; (6) SAF, containing 10% squalane, 0.4% TWEEN 80™, 5% pluronic-block polymer L121, and thr-MDP, either microfluidized into a submicron emulsion or vortexed to generate a larger particle size emulsion. (7) RIBI™) adjuvant system (RAS), (Ribi Immunochem) containing 2% squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (DETOX™); and (8) one or more mineral salts (such as an aluminum salt)+a non-toxic derivative of LPS (such as 3dMPL).Other substances that act as immunostimulating agents are disclosed in chapter 7 of ref. 112.

Where an aluminium phosphate it used, it is possible to adsorb one or more of the saccharides to the aluminium salt, but it is preferred not to do so, and this is favoured by including free phosphate ions in solution (e.g. by the use of a phosphate buffer). Where an aluminium hydroxide is used, it is preferred to adsorb the saccharides to the salt. The use of aluminium hydroxide as an adjuvant may be preferred for saccharide from serogroup A.

It is possible in compositions of the invention to adsorb some antigens to an aluminium hydroxide but to have other antigens in association with an aluminium phosphate. For tetravalent *N. meningitidis* serogroup combinations, for example, the following permutations are available:

| Serogroup | Aluminium salt (H = a hydroxide; P = a phosphate) | | | | | | | | | | | | | | |
|---|---|---|---|---|---|---|---|---|---|---|---|---|---|---|---|
| A | P | H | P | H | H | H | P | P | P | H | H | H | P | P | P | H |
| C | P | H | H | P | H | H | P | H | H | P | P | H | P | H | P | P |
| W135 | P | H | H | H | P | H | H | P | H | H | P | P | P | P | H | P |
| Y | P | H | H | H | H | P | H | H | P | P | H | P | H | P | P | P |

For trivalent *N. meningitidis* serogroup combinations, the following permutations are available:

| Serogroup | Aluminium salt (H = a hydroxide; P = a phosphate) | | | | | | | |
|---|---|---|---|---|---|---|---|---|
| C | P | H | H | H | P | P | P | H |
| W135 | P | H | H | P | H | P | H | P |
| Y | P | H | P | H | H | H | P | P |

Further Components of the Compositions

In addition to antigens described above, compositions of the invention may include meningococcal protein antigens.

Non-meningococcal and non-neisserial antigens, preferably ones that do not diminish the immune response against the meningococcal components, may also be included. Ref. 174, for instance, discloses combinations of oligosaccharides from *N. meningitidis* serogroups B and C together with the Hib saccharide. Antigens from pneumococcus, hepatitis A virus, hepatitis B virus, *B.pertussis*, diphtheria, tetanus, polio and/or *H. influenzae* are preferred. Particularly preferred antigens include:

a diphtheria antigen, such as a diphtheria toxoid [e.g. chapter 3 of ref. 175].

a tetanus antigen, such as a tetanus toxoid [e.g. chapter 4 of ref. 175].

pertussis holotoxin (PT) and filamentous haemagglutinin (FHA) from *B.pertussis*, optionally also in combination with pertactin and/or agglutinogens 2 and 3 [e.g. refs. 176 & 177].

cellular pertussis antigen.

an antigen from hepatitis A virus, such as inactivated virus [e.g. 178, 179].

an antigen from hepatitis B virus, such as the surface and/or core antigens [e.g. 179, 180], with surface antigen preferably being adsorbed onto an aluminium phosphate [181].

Preparations of *N. meningitidis* serogroup B microvesicles [182], 'native OMVs' [183], blebs or outer membrane vesicles [e.g. refs. 184 to 185 186 187 188 189 etc.]. These may be prepared from bacteria which have been genetically manipulated [190-191 192 193] e.g. to increase immunogenicity (e.g. hyper-express immunogens), to reduce toxicity, to inhibit capsular polysaccharide synthesis, to down-regulate PorA expression, etc. They may be prepared from hyperblebbing strains [194-195 196 197]. Vesicles from a non-pathogenic *Neisseria* may be included [198]. OMVs may be prepared without the use of detergents [199,200]. They may express non-Neisserial proteins on their surface [201]. They may be LPS-depleted. They may be mixed with recombinant antigens [184,202]. Vesicles from bacteria with different class I outer membrane protein subtypes may be used e.g. six different subtypes [203, 204] using two different genetically-engineered vesicle populations each displaying three subtypes, or nine different subtypes using three different genetically-engineered vesicle populations each displaying three subtypes, etc. Useful subtypes include: P1.7,16; P1.5-1,2-2; P1.19,15-1; P1.5-2,10; P1.12-1,13; P1.7-2,4; P1.22,14; P1.7-1,1; P1.18-1,3,6.

polio antigen(s) [e.g. 205, 206] such as IPV.

The mixture may comprise one or more of these further antigens, which may be detoxified where necessary (e.g. detoxification of pertussis toxin by chemical and/or genetic means).

Where a diphtheria antigen is included in the mixture it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Such DTP combinations can be used to reconstitute lyophilised conjugates.

Antigens in the mixture will typically be present at a concentration of at least 1 µg/ml each. In general, the concentration of any given antigen will be sufficient to elicit an immune response against that antigen.

As an alternative to using proteins antigens in the mixture, nucleic acid encoding the antigen may be used. Protein components of the mixture may thus be replaced by nucleic acid (preferably DNA e.g. in the form of a plasmid) that encodes the protein. Similarly, compositions of the invention may comprise proteins which mimic saccharide antigens e.g. mimotopes [207] or anti-idiotype antibodies. These may replace individual saccharine components, or may supplement them. As an example, the vaccine may comprise a peptide mimic of the MenC [208] or the MenA [209] capsular polysaccharide in place of the saccharide itself.

Compositions of the invention may include an antimicrobial, particularly when packaged in multiple dose format.

Compositions of the invention may comprise detergent (e.g. a TWEEN™ (polysorbate), such as TWEEN80™) at low levels (e.g. <0.01%).

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose [210] or trehalose [211]) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The invention provides a composition comprising conjugated capsular saccharides from at least three of serogroups A, C, W135 and Y of *N. meningitidis*, wherein the composition comprises sucrose. The saccharides are preferably oligosaccharides. The composition may contain ≤50 µg total meningococcal saccharide per dose (e.g. ≤40 µg, ≤30 µg, ≤20 µg, ≤10 µg). Preferred compositions include: serogroups A, C, W135; serogroups A, C, Y; serogroups C, W135, Y; and all four of serogroups A, C, W135 and Y. Modified MenA saccharide may be used. The composition may be in aqueous or dried (e.g. lyophilised) form. When in aqueous form, the concentration of sucrose is preferably between 5-50 mg/ml e.g. about 25 mg/ml. When in lyophilised form, it is preferred that the composition does not include an aluminium salt adjuvant. The composition may additionally comprise an antigen from one or more of: (a) serogroup B *N. meningitidis*; (b) *Haemophilus influenzae* type B; and/or (c) *Streptococcus pneumoniae*.

Immunogenicity

Compositions of the invention are immunogenic. Preferred immunogenic compositions are vaccines. Vaccines according to the invention may either be prophylactic (i.e. to prevent infection) or therapeutic (i.e. to treat disease after infection), but will typically be prophylactic.

Immunogenic compositions and vaccines of the invention will, in addition to the antigens described above, typically comprise 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose [211], lactose, lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 212.

Immunogenic compositions used as vaccines comprise an immunologically effective amount of each antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group to be treated (e.g. non-human primate, human, etc.), the capacity of the individual's immune system to synthesise antibodies, the degree of protection desired, the formulation of the vaccine, the treating doctor's assessment of the medical situation, and other relevant factors. The amount falls in a relatively broad range that can be determined through routine trials, and a typical quantity of each meningococcal saccharide antigen per dose is between 1 µg and 20 µg e.g. about 1 µg, about 2.5 µg, about 4 µg, about 5 µg, or about 10 µg (expressed as saccharide).

Immunogenicity of compositions of the invention can be determined by administering them to test subjects (e.g. children 12-16 months age, or animal models [213]) and then determining standard parameters including serum bactericidal antibodies (SBA) and ELISA titres (GMT) of total and high-avidity anti-capsule IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Administration of Compositions of the Invention

Compositions of the invention are injectable.

Parenteral injection may be subcutaneous, intraperitoneal, intravenous or intramuscular. Intramuscular administration to the thigh or the upper arm is preferred. Injection may be via a needle (e.g. a hypodermic needle), but needle-free injection may alternatively be used. A typical intramuscular dose value is 0.5 ml.

Administration may be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Administration will generally be to an animal and, in particular, human subjects can be treated. The compositions are particularly useful for vaccinating children and teenagers.

Medical Methods and Uses

The invention provides a method of raising an immune response in a patient, comprising injecting a patient with a composition of the invention. The immune response is preferably protective against meningococcal disease, and may comprise a humoral immune response and/or a cellular immune response. The patient is preferably a child.

The method may raise a booster response, in a patient that has already been primed against *N. meningitidis*.

The invention also provides the use of (i) capsular saccharides from at least two of serogroups A, C, W135 and Y of *N. meningitidis* wherein said capsular saccharides are conjugated to carrier protein(s) and/or are oligosaccharides, and (ii) an antigen from one or more of: (a) serogroup B *N. meningitidis*; (b) *Haemophilus influenzae* type B; and/or (c) *Streptococcus pneumoniae*, in the manufacture of a injectable medicament for raising an immune response in an animal. The medicament is preferably for the prevention and/or treatment of bacterial meningitis.

One way of checking efficacy of therapeutic treatment involves monitoring bacterial infection after administration of the composition of the invention. One way of checking efficacy of prophylactic treatment involves monitoring immune responses against the administered antigens after administration of the composition.

Heterologous Host

Whilst expression of polypeptides for use in compositions of the invention may take place in the native host (e.g. in a *N. meningitidis* or *S. pneumoniae*), a heterologous host is preferably used. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeast, etc.

General

The term "comprising" means "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Bacterial strains may be indicated as a subscript e.g. $741_{MC58}$ is protein 741 from strain MC58. Unless otherwise stated, proteins mentioned herein (e.g. with no subscript) are from *N. meningitidis* strain 2996, which can be taken as a 'reference' strain. It will be appreciated, however, that the invention is not in general limited by strain. As mentioned above, general references to a protein (e.g. '287', '919' etc.) may be taken to include that protein from any strain. This will typically have sequence identity to 2996 of 90% or more (eg. 91%, 92%, 93%, 94%, 95%, 96%, 97%, 98%, 99% or more). Where hybrid proteins are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq A3$ (iii) $X_1\neq X_2=X_3$ (iv) $X_1\neq X_2\neq X_3$ or (v) $X_1=X_3\neq X_2$, etc.

The term "alkyl" refers to alkyl groups in both straight and branched forms, The alkyl group may be interrupted with 1, 2 or 3 heteroatoms selected from —O—, —NH— or —S—. The alkyl group may also be interrupted with 1, 2 or 3 double and/or triple bonds. However, the term "alkyl" usually refers to alkyl groups having no heteroatom interruptions or double or triple bond interruptions. Where reference is made to $C_{1-12}$ alkyl, it is meant the alkyl group may contain any number of carbon atoms between 1 and 12 (e.g. $C_1, C_2, C_3, C_4, C_5, C_6, C_7, C_8, C_9, C_{10}, C_{11}, C_{12}$). Similarly, where reference is made to $C_{1-6}$ alkyl, it is meant the alkyl group may contain any number of carbon atoms between 1 and 6 (e.g. $C_1, C_2, C_3, C_4, C_5, C_6$).

The term "cycloalkyl" includes cycloalkyl, polycycloalkyl, and cycloalkenyl groups, as well as combinations of these with alkyl groups, such as cycloalkylalkyl groups. The cycloalkyl group may be interrupted with 1, 2 or 3 heteroatoms selected from —O—, —NH— or —S—. However, the term "cycloalkyl" usually refers to cycloalkyl groups having no heteroatom interruptions Examples of cycloalkyl groups include cyclopentyl, cyclohexyl, cyclohexenyl, cyclohexylmethyl and adamantyl groups. Where reference is made to $C_{3-12}$ cycloalkyl, it is meant that the cycloalkyl group may contain any number of carbon atoms between 3 and 12 (e.g. $C_3, C_4, C_5, C_6, C_7, C_8, C_9, C_{10}, C_{11}, C_{12}$).

The term "aryl" refers to an aromatic group, such as phenyl or naphthyl. Where reference is made to $C_{5-12}$ aryl, it is meant that the aryl group may contain any number of carbon atoms between 5 and 12 (e.g. $C_5, C_6, C_7, C_8, C_9, C_{10}, C_{11}, C_{12}$).

The term "$C_{5-12}$ aryl-$C_{1-6}$ alkyl" refers to groups such as benzyl, phenylethyl and naphthylmethyl.

Nitrogen protecting groups include silyl groups (such as TMS, TES, TBS, TIPS), acyl derivatives (such as phthalimides, trifluoroacetamides, methoxycarbonyl, ethoxycarbonyl, t-butoxycarbonyl (Boc), benzyloxycarbonyl (Z or Cbz), 9-fluorenylmethoxycarbonyl (Fmoc), 2-(trimethylsilyl)ethoxy carbonyl, 2,2,2-trichloroethoxycarbonyl (Troc)), sulfonyl derivatives (such as β-trimethylsilylethanesulfonyl (SES)), sulfenyl derivatives, $C_{1-12}$ alkyl, benzyl, benzhydryl, trityl, 9-phenylfluorenyl etc. A preferred nitrogen protecting group is Fmoc.

It will be appreciated that sugar rings can exist in open and closed form and that, whilst closed forms are shown in structural formulae herein, open forms are also encompassed by the invention.

Sequences included to facilitate cloning or purification, etc., do not necessarily contribute to the invention and may be omitted or removed.

Polypeptides of the invention can be prepared by various means (e.g. recombinant expression, purification from cell culture, chemical synthesis (at least in part), etc.) and in various forms (e.g. native, fusions, non-glycosylated, lipidated, etc.). They are preferably prepared in substantially pure form (i.e. substantially free from other *N. meningitidis* or host cell proteins).

Nucleic acid according to the invention can be prepared in many ways (e.g. by chemical synthesis (at least in part), from genomic or cDNA libraries, from the organism itself, etc.) and can take various forms (e.g. single stranded, double stranded, vectors, probes, etc.). They are preferably prepared in substantially pure form (i.e. substantially free from other *N. meningitidis* or host cell nucleic acids). The term "nucleic acid" includes DNA and RNA, and also their analogues, such as those containing modified backbones (e.g. phosphorothioates, etc.), and also peptide nucleic acids (PNA) etc. The invention includes nucleic acid comprising sequences complementary to those described above (eg. for antisense or probing purposes).

After serogroup, meningococcal classification includes serotype, serosubtype and then immunotype, and the standard nomenclature lists serogroup, serotype, serosubtype, and immunotype, each separated by a colon e.g. B:4:P1.15:

L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 41].

MODES FOR CARRYING OUT THE INVENTION

1. Meningococcal Saccharide Compositions for Human Intramuscular Administration

Oligosaccharide conjugates from MenC, MenW135, MenY and, optionally, MenA were prepared as disclosed in reference 7. These were used to prepare individual 0.5 ml doses of the following six compositions (amounts per 0.5 ml dose):

| Component | | A* | B | C* | D* | E* | F |
|---|---|---|---|---|---|---|---|
| Serogroup A oligosaccharide-$CRM_{197}$ conjugate | µg | 10 | 0 | 10 | 5 | 2.5 | 0 |
| Serogroup C oligosaccharide-$CRM_{197}$ conjugate | µg | 10 | 10 | 5 | 5 | 2.5 | 10 |
| Serogroup W135 oligosaccharide-$CRM_{197}$ conjugate | µg | 10 | 10 | 5 | 5 | 2.5 | 0 |
| Serogroup Y oligosaccharide-$CRM_{197}$ conjugate | µg | 10 | 10 | 5 | 5 | 2.5 | 0 |
| Aluminium phosphate adjuvant | mg | | | 0.3 | | | |
| Sodium chloride | mg | | | 4.5 | | | |
| Mannitol | mg | | | 7.5 | | | |
| Sodium phosphate monobasic (pH 7.6) | mg | | | 0.69 | | | |
| Potassium dihydrogen phosphate | mg | | | 0.34 | | | |
| Tween ™ 80 | mg | | | 0.025 | | | |

*The serogroup A component was in lyophilised form and was diluted with a CWY liquid composition to give the final ACWY composition.

These vaccines are administered by intramuscular injection in the thigh region to toddlers aged 12-16 months, either in a single dose (which is effective for Menjugate™ in children >12 months) or with a second injection 4 weeks later. Serum BCA and IgG can be compared pre-vaccination and post-vaccination (e.g at 4 weeks, and then at 8 weeks if two doses are received).

2. Two-Vial Composition

Conjugates for human use were prepared in two separate vials. Vial 1 contained a lyophilised powder of MenA conjugate, with sucrose and potassium dihydrogen phosphate. Vial 2 contained the MenC, MenW135 and MenY conjugates, with sodium chloride, polysorbate 80, sodium phosphate buffer, and an optional aluminium phosphate adjuvant, which is present in suspension. Prior to use, vial 1 is reconstituted with 0.6 ml liquid from vial 2, to give 0.5 ml available for administration.

Three doses were prepared. In reconstituted form, vaccines contained antigens as follows:

| Component | Quantity per 0.5 ml dose |
|---|---|
| Serogroup A conjugate | 10 µg saccharide + 12.5-33 µg $CRM_{197}$ |
| | OR 5 µg saccharide + 6.25-16.5 µg $CRM_{197}$ |
| | OR 2.5 µg saccharide + 3.125-8.25 µg $CRM_{197}$ |
| Serogroup C conjugate | 10 µg saccharide + 12.5-25 µg $CRM_{197}$ |
| | OR 5 µg saccharide + 6.25-12.5 µg $CRM_{197}$ |
| | OR 2.5 µg saccharide + 3.125-6.25 µg $CRM_{197}$ |
| Serogroup W135 conjugate | 10 µg saccharide + 6.6-20 µg $CRM_{197}$ |
| | OR 5 µg saccharide + 3.3-10 µg $CRM_{197}$ |
| | OR 2.5 µg saccharide + 1.65-5 µg $CRM_{197}$ |
| Serogroup Y conjugate | 10 µg saccharide + 6.6-20 µg $CRM_{197}$ |
| | OR 5 µg saccharide + 3.3-10 µg $CRM_{197}$ |
| | OR 2.5 µg saccharide + 1.65-5 µg $CRM_{197}$ |

In reconstituted form, vaccines contained other components as follows:

| Component | Quantity per 0.5 ml dose | |
|---|---|---|
| Aluminium phosphate adjuvant | 0.3 mg as $Al^{3+}$ | zero |
| Sodium dihydrogen phosphate | 1 mM | 2.5 mM |
| Disodium hydrogen phosphate dihydrate | 9 mM | 7.5 mM |
| Sodium phosphate buffer | | 10 mM |
| Potassium dihydrogen phosphate | | 5 mM |
| Tween ™ 80 (surfactant) | | 0.025 mg |
| Sodium chloride (tonicity) | | 4.5 mg |
| Sucrose (lyophilisation & tonicity) | | 12.5 mg |
| Water for injection | | To final volume |

Six vaccines were thus available—three different doses (10, 20 or 40 µg total saccharide), each with or without aluminium phosphate adjuvant.

The adjuvanted vaccine with the highest saccharide dose was administered to healthy human subjects aged 18-45. For comparison, control subjects received either (a) the vial 1 (reconstituted in buffer) and vial 2 products in different arms at the same time, or (b) Mencevax™. Each patient group contains 30 people.

Blood was collected before and 28 days after vaccination to evaluate the immune response and to collect laboratory safety parameters (complete blood count, blood chemistry analyses, liver and renal function tests and urinalysis). The vaccine was well tolerated, with no unexpected adverse reactions. No significant abnormal changes in laboratory parameters occurred during the study.

Serogroup A, C, W-135, Y specific SBA and IgG (measured by ELISA) were determined in the serum samples. SBA titres were expressed as the reciprocal of the final serum dilution giving ≥50% killing at 60 minutes. For IgG measurement, a modified ELISA was performed to assay high avidity antibodies. For the detection of functional antibodies, SBAs with two different exogenous sources of complement were used: a baby rabbit complement source and a human complement source.

The high avidity IgG results were as follows (mean GMC (µg/mL) with 95% confidence intervals):

| | | Vaccine Group | | |
|---|---|---|---|---|
| Serogroup | Serum | ACWY | A + CWY | Mencevax ™ |
| A | Pre | 0.67 (0.3-1.2) | 0.85 (0.4-1.5) | 0.45 (0.2-0.8) |
| | Post | 10 (6.6-16) | 14 (8.8-22) | 9.8 (6.2-15) |
| C | Pre | 0.21 (0.1-0.3) | 0.13 (0.07-0.2) | 0.16 (0.1-0.2) |
| | Post | 7.7 (4.7-13) | 5.2 (3.19-8.46) | 8.5 (5.2-14) |
| W-135 | Pre | 0.21 (0.1-0.3) | 0.2 (0.1-0.3) | 0.29 (0.19-0.4) |
| | Post | 12 (6.5-21) | 9 (5.5-18) | 6.7 (3.7-12) |
| Y | Pre | 0.35 (0.2-0.5) | 0.31 (0.1-0.5) | 0.57 (0.3-0.9) |
| | Post | 18 (12-29) | 21 (13-33) | 20 (12-31) |

The SBA results were as follows (% responders and mean GMT, both with 95% CI):

| Sero-group | Vaccine Group | Rabbit Complement SBA | | Human Complement SBA | |
|---|---|---|---|---|---|
| | | Titres ≥1:128 (%) | GMT | Titres ≥1:4 (%) | GMT |
| A | ACWY | 93 (78-99) | 989 (558-1754) | 90 (73-98) | 42 (23-76) |
| | A + CWY | 97 (83-100) | 2566 (1448-4549) | 97 (83-100) | 66 (36-119) |
| | MENCEVAX ™ | 100 (88-100) | 3132 (1767-5552) | 83 (65-94) | 28 (15-50) |
| C | ACWY | 97 (82-100) | 4480 (2455-8176) | 100 (88-100) | 213 (106-427) |
| | A + CWY | 100 (88-100) | 3794 (2100-6855) | 100 (88-100) | 162 (80-325) |
| | MENCEVAX ™ | 93 (78-99) | 3829 (2119-6918) | 100 (88-100) | 223 (111-448) |
| W-135 | ACWY | 100 (88-100) | 10343 (5988-17865) | 100 (88-100) | 248 (123-500) |
| | A + CWY | 100 (88-100) | 10376 (6007-17923) | 93 (78-99) | 142 (71-287) |
| | MENCEVAX ™ | 100 (88-100) | 6795 (3934-11737) | 97 (83-100) | 99 (49-199) |
| Y | ACWY | 100 (88-100) | 22075 (14689-33175) | 100 (88-100) | 263 (151-457) |
| | A + CWY | 100 (88-100) | 24034 (15993-36120) | 100 (88-100) | 162 (194-588) |
| | MENCEVAX ™ | 100 (88-100) | 14630 (9735-21987) | 100 (88-100) | 198 (114-344) |

For each serogroup and in each vaccine group (ACWY, A+CWY and MENCEVAX™ control) the high avidity ELISA anti-capsular IgG GMCs and the SBA GMT measured with both rabbit and human complement assay, increased after injection. At day 29 after vaccine injection, the percentage of subjects with human complement SBA titers ≥1:4 for each serogroup ranged between 90%-100% in the conjugate vaccines and between 83%-100% in the control group. Using the rabbit complement source, the percentage of subjects with SBA titers ≥1:128 for each serogroup ranged between 93%-100% for the conjugate vaccines and between 90%-100% for the control group.

Overall, immune responses (GMC and GMT) were better in the conjugate groups than in the MENCEVAX™ control group. The improvement was particularly seen for serogroup W-135. The conjugate vaccines of the invention are thus safe, well tolerated and induce functional immune responses equal to or better than those observed following immunisation with a licensed tetravalent polysaccharide vaccine.

3. Use of Modified MenA Saccharide

Capsular polysaccharide was purified from MenA and was hydrolysed to give MenA oligosaccharide. The polysaccharide (2 g) was hydrolyzed at 50° C. in 50 mM sodium acetate buffer, pH 4.75, at a polysaccharide concentration of 10 mg/mL for about 4 hours [73]. After hydrolysis, the solution was dried by rotary evaporation.

The oligosaccharide was activated using the following reaction scheme:

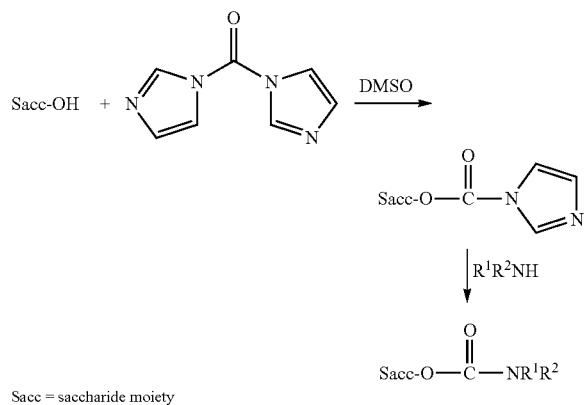

Sacc = saccharide moiety

The oligosaccharide was dissolved in DMSO to give a saccharide concentration of 10 mg/mL. According to a molar ratio of oligosaccharide:CDI being 1:20, 21.262 g of CDI was then added and the reaction mixture stirred for 16 hours at room temperature. The resulting MenA-CDI compound was purified by selective precipitation in a 80:20 (v/v) acetone:DMSO mixture followed by centrifugation. The efficiency of the activation reaction was calculated to be about 67.9% by determining the ratio of free imidazole to bonded imidazole.

In the second reaction step, the MenA-CDI oligosaccharide was solubilised in DMSO at a saccharide concentration of about 10 mg/mL. According to a molar ratio of MenA-CDI unit:DMA being 1:100, 36.288 g of 99% dimethylamine hydrochloride (i.e. $R^1$ & $R^2$=Me) was added and the reaction mixture stirred for 16 hours at room temperature. The reaction product was freeze-dried and re-solubilised in 10 mg/mL water solution.

To remove the low molecular weight reaction reagent (in particular the dimethylamine (DMA)) from the oligosaccharide preparation, a dialysis step was performed through a 3.5 kDa MWCO membrane (Spectra/Por™). Four dialysis steps were carried out: (i) 16 hours against 2 L of 1 M sodium chloride (dialysis factor 1:20), (ii) 16 hours against 2 L of 0.5 M sodium chloride (dialysis factor 1:20), (iii) and (iv) 16 hours against 2 L of WFI (dialysis factor 1:20). To improve the purification a diafiltration step was also performed through a 1 kDa MWCO membrane (Centricon™)

The purified MenA-CDI-DMA product was buffered at pH 6.5 in 25 mM L-histidine (Fluka™)

For preparing conjugates of the modified MenA saccharide (MenA-CDI-DMA), the overall process was as follows:
- hydrolysis of the polysaccharide to give oligosaccharide fragments
- sizing of the oligosaccharide fragments
- reductive amination of terminal aldehyde groups on the sized oligosaccharides
- protection of terminal —$NH_2$ groups by Fmoc group before the CDI reaction
- intrinsic de-protection of —$NH_2$ groups during the DMA reaction
- activation of terminal —$NH_2$ groups by SIDEA (N-hydroxysuccinimide adipic acid)
- covalent attachment to $CRM_{197}$ protein.

The modified MenA oligosaccharide conjugate was much more resistant to hydrolysis than its natural counterpart at elevated temperatures. After 28 days at 37° C., for instance, the percentage of released saccharide is 6.4% for the modified oligosaccharide vs. 23.5% for the natural antigen.

Moreover, the titres induced by the modified oligosaccharides are not significantly lower than those obtained using the native sugar structures.

The modified MenA conjugate is combined with MenC, MenW135 and MenY conjugates as a substitute for the conjugate of unmodified oligosaccharide.

4. Addition of MenB Antigens

Prior to reconstitution of the lyophilised MenA conjugate as described above, MenB antigens ΔG287-953 (SEQ ID NO: 7), 936-ΔG741 (SEQ ID NO: 8) and NadA (SEQ ID NO: 2) are added to the highest-dose liquid C-W135-Y mixture to give a final concentration of 20 μg/dose of each of the three polypeptides. The reconstituted vaccine thus contains the following antigens:

| Component | Quantity per 0.5 ml dose |
| --- | --- |
| Serogroup A conjugate | 10 μg saccharide + 12.5-33 μg $CRM_{197}$ |
| Serogroup C conjugate | 10 μg saccharide + 12.5-25 μg $CRM_{197}$ |
| Serogroup W135 conjugate | 10 μg saccharide + 6.6-20 μg $CRM_{197}$ |
| Serogroup Y conjugate | 10 μg saccharide + 6.6-20 μg $CRM_{197}$ |
| ΔG287-953 | 20 μg polypeptide |
| 936-ΔG741 | 20 μg polypeptide |
| NadA | 20 μg polypeptide |

5. Addition of Hib Antigen

Lyophilised HbOC conjugate is mixed with the lyophilised MenA conjugate and both are reconstituted together by liquid C-W135-Y mixture to give following vaccine:

| Component | Quantity per 0.5 ml dose |
| --- | --- |
| Serogroup A conjugate | 10 μg saccharide + 12.5-33 μg $CRM_{197}$ |
| Serogroup C conjugate | 10 μg saccharide + 12.5-25 μg $CRM_{197}$ |
| Serogroup W135 conjugate | 10 μg saccharide + 6.6-20 μg $CRM_{197}$ |
| Serogroup Y conjugate | 10 μg saccharide + 6.6-20 μg $CRM_{197}$ |
| HbOC Hib conjugate | 10 μg saccharide + 2-5 μg $CRM_{197}$ |

6. Addition of Pneumococcal Antigens

Prior to reconstitution of the lyophilised MenA conjugate as described above, pneumococcal conjugate antigens are added to the medium-dose liquid C-W135-Y mixture to give a final concentration of 2 μg/dose of each of the serotypes (double for serotype 6B). The reconstituted vaccine thus contains the following antigens:

| Component | Quantity per 0.5 ml dose |
| --- | --- |
| Serogroup A conjugate | 5 μg saccharide + 6.25-16.5 μg $CRM_{197}$ |
| Serogroup C conjugate | 5 μg saccharide + 6.25-12.5 μg $CRM_{197}$ |
| Serogroup W135 conjugate | 5 μg saccharide + 3.3-10 μg $CRM_{197}$ |
| Serogroup Y conjugate | 5 μg saccharide + 3.3-10 μg $CRM_{197}$ |
| Pneumococcus serotype 4 conjugate | 2 μg saccharide + 2.5 μg $CRM_{197}$ |
| Pneumococcus serotype 9V conjugate | 2 μg saccharide + 2.5 μg $CRM_{197}$ |
| Pneumococcus serotype 14 conjugate | 2 μg saccharide + 2.5 μg $CRM_{197}$ |
| Pneumococcus serotype 18C conjugate | 2 μg saccharide + 2.5 μg $CRM_{197}$ |
| Pneumococcus serotype 19F conjugate | 2 μg saccharide + 2.5 μg $CRM_{197}$ |
| Pneumococcus serotype 23F conjugate | 2 μg saccharide + 2.5 μg $CRM_{197}$ |
| Pneumococcus serotype 6B conjugate | 4 μg saccharide + 5 μg $CRM_{197}$ |

It will be understood that the invention has been described by way of example only and modifications may be made whilst remaining within the scope and spirit of the invention.

REFERENCES

The Contents of which are Hereby Incorporated in Full

[1] Chapter 28 of Vaccines (Plotkin & Orenstein) 3rd edition (1999) ISBN 0-7216-7443-7.
[2] Armand et al. (1982) *J. Biol. Stand.* 10:335-339.
[3] Cadoz et al. (1985) *Vaccine* 3:340-342.
[4] MMWR (1997) 46(RR-5) 1-10.
[5] Baldaic et al. (1983) *Infect. Immun.* 42:599-604.
[6] WO02/058737.
[7] WO03/007985.
[8] Rennels et al. (2002) *Pediatr Infect Dis J* 21:978-979.
[9] Campbell et al. (2002) *J Infect Dis* 186:1848-1851.
[10] Costantino et al. (1992) *Vaccine* 10:691-698.
[11] Jones (2001) *Curr Opin Investig Drugs* 2:47-49.
[12] WO02/00249.
[13] WO97/28273.
[14] Lieberman et al. (1996) *JAMA* 275:1499-1503.
[15] Frash (1990) p. 123-145 of *Advances in Biotechnological Processes* vol. 13 (eds. Mizrahi & Van Wezel)
[16] Inzana (1987) *Infect. Immun.* 55:1573-1579.
[17] Kandil et al. (1997) *Glycoconj J* 14:13-17.
[18] Berkin et al. (2002) *Chemistry* 8:4424-4433.
[19] WO03/080678.
[20] WO98/08543.
[21] Tettelin et al. (2000) *Science* 287:1809-1815.
[22] Pizza et al. (2000) *Science* 287:1816-1820.
[23] WO99/24578.
[24] WO99/36544.
[25] WO99/57280.
[26] WO00/22430.
[27] WO00/66791.
[28] WO00/66741.
[29] WO01/64920.
[30] WO01/64922.
[31] WO03/020756.
[32] UK patent applications 0223741.0, 0305831.0 & 0309115.4, and international application PCT/IB03/04848.
[33] Comanducci et al. (2002) *J. Exp. Med.* 195:1445-1454.
[34] WO03/010194.
[35] Parkhill et al. (2000) *Nature* 404:502-506.
[36] International patent application PCT/IB03/06320.
[37] WO03/063766.
[38] Masignani et al. (2003) *J Exp Med* 197:789-799.
[39] http://neisseria.org/nm/typing/mlst/
[40] Pettersson et al. (1994) *Microb Pathog* 17(6):395-408.
[41] Maiden et al. (1998) *PNAS USA* 95:3140-3145.
[42] Welsch et al. (2002) Thirteenth International Pathogenic *Neisseria* Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[43] Santos et al. (2002) Thirteenth International Pathogenic *Neisseria* Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[44] Lindberg (1999) *Vaccine* 17 Suppl 2:S28-36.

[45] Buttery & Moxon (2000) *J R Coll Physicians Lond* 34:163-168.
[46] Ahmad & Chapnick (1999) *Infect Dis Clin North Am* 13:113-33, vii.
[47] Goldblatt (1998) *J. Med. Microbiol.* 47:563-567.
[48] European patent 0477508.
[49] U.S. Pat. No. 5,306,492.
[50] WO98/42721.
[51] Dick et al. in *Conjugate Vaccines* (eds. Cruse et al.) Karger, Basel, 1989, 10:48-114.
[52] Hermanson *Bioconjugate Techniques*, Academic Press, San Diego (1996) ISBN: 0123423368.
[53] Kanra et al. (1999) *The Turkish Journal of Paediatrics* 42:421-427.
[54] Ravenscroft et al. (2000) *Dev Biol* (Basel) 103: 35-47.
[55] WO97/00697.
[56] WO96/37222; U.S. Pat. No. 6,333,036.
[57] Watson (2000) *Pediatr Infect Dis J* 19:331-332.
[58] Rubin (2000) *Pediatr Clin North Am* 47:269-285, v.
[59] Jedrzejas (2001) *Microbiol Mol Biol Rev* 65:187-207.
[60] Zielen et al. (2000) *Infect. Immun.* 68:1435-1440.
[61] Darkes & Plosker (2002) *Paediatr Drugs* 4:609-630.
[62] Tettelin et al. (2001) *Science* 293:498-506.
[63] Hoskins et al (2001) *J Bacteriol* 183:5709-5717.
[64] Rappuoli (2000) *Curr Opin Microbiol* 3:445-450
[65] Rappuoli (2001) *Vaccine* 19:2688-2691.
[66] Masignani et al. (2002) *Expert Opin Biol Ther* 2:895-905.
[67] Mora et al. (2003) *Drug Discov Today* 8:459-464.
[68] Wizemann et al. (2001) *Infect Immun* 69:1593-1598.
[69] Rigden et al. (2003) *Crit Rev Biochem Mol Biol* 38:143-168.
[70] WO02/22167.
[71] Nilsson & Svensson (1979) *Carbohydrate Research* 69: 292-296)
[72] Ravenscroft et al. (1999) *Vaccine* 17:2802-2816.
[73] Costantino et al. (1999) *Vaccine* 17:1251-1263.
[74] Ramsay et al. (2001) *Lancet* 357(9251):195-196.
[75] Anonymous (January 2002) *Research Disclosure*, 453077.
[76] Anderson (1983) *Infect Immun* 39(1):233-238.
[77] Anderson et al. (1985) *J Clin Invest* 76(1):52-59.
[78] EP-A-0372501.
[79] EP-A-0378881.
[80] EP-A-0427347.
[81] WO93/17712
[82] WO94/03208.
[83] WO98/58668.
[84] EP-A-0471177.
[85] WO91/01146
[86] Falugi et al. (2001) *Eur J Immunol* 31:3816-3824.
[87] EP-A-0594610.
[88] WO00/56360.
[89] WO02/091998.
[90] WO01/72337
[91] WO00/61761.
[92] WO99/42130
[93] WO96/40242
[94] Lees et al. (1996) *Vaccine* 14:190-198.
[95] WO95/08348.
[96] U.S. Pat. No. 4,882,317
[97] U.S. Pat. No. 4,695,624
[98] Porro et al. (1985) *Mol Immunol* 22:907-919.
[99] EP-A-0208375
[100] WO00/10599
[101] Gever et al. Med. Microbiol. Immunol, 165: 171-288 (1979).
[102] U.S. Pat. No. 4,057,685.
[103] U.S. Pat. Nos. 4,673,574; 4,761,283; 4,808,700.
[104] U.S. Pat. No. 4,459,286.
[105] U.S. Pat. No. 4,965,338
[106] U.S. Pat. No. 4,663,160.
[107] U.S. Pat. No. 4,761,283
[108] U.S. Pat. No. 4,356,170
[109] Lei et al. (2000) *Dev Biol* (Basel) 103:259-264.
[110] WO00/38711; U.S. Pat. No. 6,146,902.
[111] WO03/009869.
[112] *Vaccine Design* . . . (1995) eds. Powell & Newman. ISBN: 030644867X. Plenum.
[113] WO00/23105.
[114] U.S. Pat. No. 5,057,540.
[115] WO96/33739.
[116] EP-A-0109942.
[117] WO96/11711.
[118] WO00/07621.
[119] Barr et al. (1998) *Advanced Drug Delivery Reviews* 32:247-271.
[120] Sjolanderet et al. (1998) *Advanced Drug Delivery Reviews* 32:321-338.
[121] Niikura et al. (2002) *Virology* 293:273-280.
[122] Lenz et al. (2001) *J Immunol* 166:5346-5355.
[123] Pinto et al. (2003) *J Infect Dis* 188:327-338.
[124] Gerber et al. (2001) *Virol* 75:4752-4760.
[125] WO03/024480
[126] WO03/024481
[127] Gluck et al. (2002) *Vaccine* 20:B10-B16.
[128] EP-A-0689454.
[129] Johnson et al. (1999) *Bioorg Med Chem Lett* 9:2273-2278.
[130] Evans et al. (2003) *Expert Rev Vaccines* 2:219-229.
[131] Meraldi et al. (2003) *Vaccine* 21:2485-2491.
[132] Pajak et al. (2003) *Vaccine* 21:836-842.
[133] Kandimalla et al. (2003) *Nucleic Acids Research* 31:2393-2400.
[134] WO02/26757.
[135] WO99/62923.
[136] Krieg (2003) *Nature Medicine* 9:831-835.
[137] McCluskie et al. (2002) *FEMS Immunology and Medical Microbiology* 32:179-185.
[138] WO98/40100.
[139] U.S. Pat. No. 6,207,646.
[140] U.S. Pat. No. 6,239,116.
[141] U.S. Pat. No. 6,429,199.
[142] Kandimalla et al. (2003) *Biochemical Society Transactions* 31 (part 3):654-658.
[143] Blackwell et al. (2003) *J Immunol* 170:4061-4068.
[144] Krieg (2002) *Trends Immunol* 23:64-65.
[145] WO01/95935.
[146] Kandimalla et al. (2003) *BBRC* 306:948-953.
[147] Bhagat et al. (2003) *BBRC* 300:853-861.
[148] WO03/035836.
[149] WO95/17211.
[150] WO98/42375.
[151] Beignon et al. (2002) *Infect Immun* 70:3012-3019.
[152] Pizza et al. (2001) *Vaccine* 19:2534-2541.
[153] Pizza et al. (2000) *Int J Med Microbiol* 290:455-461.
[154] Scharton-Kersten et al. (2000) *Infect Immun* 68:5306-5313.
[155] Ryan et al. (1999) *Infect Immun* 67:6270-6280.
[156] Partidos et al. (1999) *Immunol Lett* 67:209-216.
[157] Peppoloni et al. (2003) *Expert Rev Vaccines* 2:285-293.
[158] Pine et al. (2002) *J Control Release* 85:263-270.

[159] Domenighini et al. (1995) *Mol Microbiol* 15:1165-1167.
[160] WO99/40936.
[161] WO99/44636.
[162] Singh et al] (2001) *J Cont Release* 70:267-276.
[163] WO99/27960.
[164] U.S. Pat. No. 6,090,406
[165] U.S. Pat. No. 5,916,588
[166] EP-A-0626169.
[167] WO99/52549.
[168] WO01/21207.
[169] WO01/21152.
[170] Andrianov et al. (1998) *Biomaterials* 19:109-115.
[171] Payne et al. (1998) *Adv Drug Delivery Review* 31:185-196.
[172] Stanley (2002) *Clin Exp Dermatol* 27:571-577.
[173] Jones (2003) *Curr Opin Investig Drugs* 4:214-218.
[174] WO96/14086.
[175] Vaccines (eds. Plotkin & Mortimer), 1988. ISBN: 0-7216-1946-0
[176] Gustafsson et al. (1996) *N. Engl. J. Med.* 334:349-355.
[177] Rappuoli et al. (1991) *TIBTECH* 9:232-238.
[178] Bell (2000) *Pediatr Infect Dis J* 19:1187-1188.
[179] Iwarson (1995) *APMIS* 103:321-326.
[180] Gerlich et al. (1990) Vaccine 8 Suppl:S63-68 & 79-80.
[181] WO93/24148.
[182] WO02/09643.
[183] Katial et al. (2002) *Infect Immun* 70:702-707.
[184] WO01/52885.
[185] European patent 0301992.
[186] Bjune et al. (1991) *Lancet* 338(8775):1093-1096.
[187] Fukasawa et al. (1999) *Vaccine* 17:2951-2958.
[188] WO02/09746.
[189] Rosenqvist et al. (1998) *Dev. Biol. Stand.* 92:323-333.
[190] WO01/09350.
[191] European patent 0449958.
[192] EP-A-0996712.
[193] EP-A-0680512.
[194] WO02/062378.
[195] WO99/59625.
[196] U.S. Pat. No. 6,180,111.
[197] WO01/34642.
[198] WO03/051379.
[199] U.S. Pat. No. 6,558,677
[200] PCT/IB03/04293.
[201] WO02/062380.
[202] WO00/25811.
[203] Peeters et al. (1996) *Vaccine* 14:1008-1015.
[204] Vermont et al. (2003) *Infect Immun* 71:1650-1655.
[205] Sutter et al. (2000) *Pediatr Clin North Am* 47:287-308.
[206] Zimmerman & Spann (1999) *Am Fam Physician* 59:113-118, 125-126.
[207] Charalambous & Feavers (2001) *J Med Microbiol* 50:937-939.
[208] Westerink (2001) *Int Rev Immunol* 20:251-261.
[209] Grothaus et al. (2000) *Vaccine* 18:1253-1263.
[210] Paoletti et al. (2001) *Vaccine* 19:2118-2126.
[211] WO00/56365.
[212] Gennaro (2000) *Remington: The Science and Practice of Pharmacy.* 20th ed ISBN: 0683306472
[213] WO01/30390.

The invention claimed is:

1. A kit comprising
   (a) a lyophilized capsular saccharide of *Neisseria meningitidis* serogroup A conjugated to a carrier protein and
   (b) liquid capsular saccharides of *Neisseria meningitidis* serogroups C, W135 and Y each conjugated to a carrier protein,
   wherein each of the conjugates is a separate conjugate for each of the serogroups A, C, Y and W135 and wherein reconstitution of the lyophilized capsular saccharide conjugate of the serogroup A *Neisseria meningitidis* with the liquid capsular saccharide conjugates of the serogroups C, Y and W135 *Neisseria meningitidis* produces an injectable composition comprising between about 10 micrograms and 25 micrograms of the capsular saccharides per dose of the composition and wherein the capsular saccharides of the *Neisseria meningitidis* serogroups A, C, W135 and Y are present at a 2:1:1:1 capsular saccharide weight ratio.

2. The kit of claim 1, wherein the capsular saccharide of *Neisseria meningtidis* serogroup A is modified so that one or more hydroxyl groups of the capsular saccharide have been replaced with blocking groups.

* * * * *

SEQUENCE LISTING

<160> NUMBER OF SEQ ID NOS: 12

<210> SEQ ID NO 1
<211> LENGTH: 350
<212> TYPE: PRT
<213> ORGANISM: Neisseria meningitidis

<400> SEQUENCE: 1

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Ala Tyr Asn Asn Gly Gln Glu Ile
            35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
                100                 105                 110

Ser Glu Ile Glu Lys Leu Thr Thr Lys Leu Ala Asp Thr Asp Ala Ala
            115                 120                 125

Leu Ala Asp Thr Asp Ala Ala Leu Asp Ala Thr Thr Asn Ala Leu Asn
        130                 135                 140

Lys Leu Gly Glu Asn Ile Thr Thr Phe Ala Glu Glu Thr Lys Thr Asn
145                 150                 155                 160
```

```
Ile Val Lys Ile Asp Glu Lys Leu Glu Ala Val Ala Asp Thr Val Asp
            165                 170                 175

Lys His Ala Glu Ala Phe Asn Asp Ile Ala Asp Ser Leu Asp Glu Thr
        180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
        210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
            245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
        290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
            325                 330                 335

Gln Ala Ala Leu Ser Gly Leu Phe Gln Pro Tyr Asn Val Gly
            340                 345                 350

<210> SEQ ID NO 2
<211> LENGTH: 327
<212> TYPE: PRT
<213> ORGANISM: Neisseria meningitidis

<400> SEQUENCE: 2

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
            85                  90                  95

Thr Lys Leu Ala Asp Thr Asp Ala Ala Leu Ala Asp Thr Asp Ala Ala
        100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
        130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
            165                 170                 175

Val Lys Thr Ala Asn Glu Ala Lys Gln Thr Ala Glu Glu Thr Lys Gln
            180                 185                 190
```

```
Asn Val Asp Ala Lys Val Lys Ala Glu Thr Ala Ala Gly Lys Ala
        195                 200                 205

Glu Ala Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
                260                 265                 270

Glu Lys Leu Asp Thr Arg Leu Ala Ser Glu Lys Ser Ile Ala Asp
                275                 280                 285

His Asp Thr Arg Leu Asn Gly Leu Asp Lys Thr Val Ser Asp Leu Arg
        290                 295                 300

Lys Glu Thr Arg Gln Gly Leu Ala Glu Gln Ala Leu Ser Gly Leu
305                 310                 315                 320

Phe Gln Pro Tyr Asn Val Gly
                325

<210> SEQ ID NO 3
<211> LENGTH: 248
<212> TYPE: PRT
<213> ORGANISM: Neisseria meningitidis

<400> SEQUENCE: 3

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
```

```
                225                 230                 235                 240

His Ile Gly Leu Ala Ala Lys Gln
                245

<210> SEQ ID NO 4
<211> LENGTH: 179
<212> TYPE: PRT
<213> ORGANISM: Neisseria meningitidis

<400> SEQUENCE: 4

Val Ser Ala Val Ile Gly Ser Ala Ala Gly Ala Lys Ser Ala Val
1               5                   10                  15

Asp Arg Arg Thr Thr Gly Ala Gln Thr Asp Asp Asn Val Met Ala Leu
                20                  25                  30

Arg Ile Glu Thr Thr Ala Arg Ser Tyr Leu Arg Gln Asn Asn Gln Thr
            35                  40                  45

Lys Gly Tyr Thr Pro Gln Ile Ser Val Val Gly Tyr Asn Arg His Leu
        50                  55                  60

Leu Leu Leu Gly Gln Val Ala Thr Glu Gly Glu Lys Gln Phe Val Gly
65                  70                  75                  80

Gln Ile Ala Arg Ser Glu Gln Ala Ala Glu Gly Val Tyr Asn Tyr Ile
                85                  90                  95

Thr Val Ala Ser Leu Pro Arg Thr Ala Gly Asp Ile Ala Gly Asp Thr
            100                 105                 110

Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
    130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 5
<211> LENGTH: 168
<212> TYPE: PRT
<213> ORGANISM: Neisseria meningitidis

<400> SEQUENCE: 5

Ala Thr Tyr Lys Val Asp Glu Tyr His Ala Asn Ala Arg Phe Ala Ile
1               5                   10                  15

Asp His Phe Asn Thr Ser Thr Asn Val Gly Gly Phe Tyr Gly Leu Thr
                20                  25                  30

Gly Ser Val Glu Phe Asp Gln Ala Lys Arg Asp Gly Lys Ile Asp Ile
            35                  40                  45

Thr Ile Pro Ile Ala Asn Leu Gln Ser Gly Ser Gln His Phe Thr Asp
        50                  55                  60

His Leu Lys Ser Ala Asp Ile Phe Asp Ala Ala Gln Tyr Pro Asp Ile
65                  70                  75                  80

Arg Phe Val Ser Thr Lys Phe Asn Phe Asn Gly Lys Lys Leu Val Ser
                85                  90                  95

Val Asp Gly Asn Leu Thr Met His Gly Lys Thr Ala Pro Val Lys Leu
            100                 105                 110

Lys Ala Glu Lys Phe Asn Cys Tyr Gln Ser Pro Met Glu Lys Thr Glu
        115                 120                 125
```

```
Val Cys Gly Gly Asp Phe Ser Thr Thr Ile Asp Arg Thr Lys Trp Gly
            130                 135                 140
Met Asp Tyr Leu Val Asn Val Gly Met Thr Lys Ser Val Arg Ile Asp
145                 150                 155                 160
Ile Gln Ile Glu Ala Ala Lys Gln
                165

<210> SEQ ID NO 6
<211> LENGTH: 464
<212> TYPE: PRT
<213> ORGANISM: Neisseria meningitidis

<400> SEQUENCE: 6

Ser Pro Asp Val Lys Ser Ala Asp Thr Leu Ser Lys Pro Ala Ala Pro
1               5                   10                  15
Val Val Ser Glu Lys Glu Thr Glu Ala Lys Glu Asp Ala Pro Gln Ala
            20                  25                  30
Gly Ser Gln Gly Gln Gly Ala Pro Ser Ala Gln Gly Ser Gln Asp Met
        35                  40                  45
Ala Ala Val Ser Glu Glu Asn Thr Gly Asn Gly Gly Ala Val Thr Ala
    50                  55                  60
Asp Asn Pro Lys Asn Glu Asp Glu Val Ala Gln Asn Asp Met Pro Gln
65                  70                  75                  80
Asn Ala Ala Gly Thr Asp Ser Ser Thr Pro Asn His Thr Pro Asp Pro
                85                  90                  95
Asn Met Leu Ala Gly Asn Met Glu Asn Gln Ala Thr Asp Ala Gly Glu
            100                 105                 110
Ser Ser Gln Pro Ala Asn Gln Pro Asp Met Ala Asn Ala Ala Asp Gly
        115                 120                 125
Met Gln Gly Asp Asp Pro Ser Ala Gly Gly Gln Asn Ala Gly Asn Thr
    130                 135                 140
Ala Ala Gln Gly Ala Asn Gln Ala Gly Asn Asn Gln Ala Ala Gly Ser
145                 150                 155                 160
Ser Asp Pro Ile Pro Ala Ser Asn Pro Ala Pro Ala Asn Gly Gly Ser
                165                 170                 175
Asn Phe Gly Arg Val Asp Leu Ala Asn Gly Val Leu Ile Asp Gly Pro
            180                 185                 190
Ser Gln Asn Ile Thr Leu Thr His Cys Lys Gly Asp Ser Cys Ser Gly
        195                 200                 205
Asn Asn Phe Leu Asp Glu Glu Val Gln Leu Lys Ser Glu Phe Glu Lys
    210                 215                 220
Leu Ser Asp Ala Asp Lys Ile Ser Asn Tyr Lys Lys Asp Gly Lys Asn
225                 230                 235                 240
Asp Lys Phe Val Gly Leu Val Ala Asp Ser Val Gln Met Lys Gly Ile
                245                 250                 255
Asn Gln Tyr Ile Ile Phe Tyr Lys Pro Lys Pro Thr Ser Phe Ala Arg
            260                 265                 270
Phe Arg Arg Ser Ala Arg Ser Arg Arg Ser Leu Pro Ala Glu Met Pro
        275                 280                 285
Leu Ile Pro Val Asn Gln Ala Asp Thr Leu Ile Val Asp Gly Glu Ala
    290                 295                 300
Val Ser Leu Thr Gly His Ser Gly Asn Ile Phe Ala Pro Glu Gly Asn
305                 310                 315                 320
Tyr Arg Tyr Leu Thr Tyr Gly Ala Glu Lys Leu Pro Gly Gly Ser Tyr
```

```
              325                 330                 335
Ala Leu Arg Val Gln Gly Glu Pro Ala Lys Gly Glu Met Leu Ala Gly
            340                 345                 350

Ala Ala Val Tyr Asn Gly Glu Val Leu His Phe His Thr Glu Asn Gly
            355                 360                 365

Arg Pro Tyr Pro Thr Arg Gly Arg Phe Ala Ala Lys Val Asp Phe Gly
            370                 375                 380

Ser Lys Ser Val Asp Gly Ile Ile Asp Ser Gly Asp Leu His Met
385                 390                 395                 400

Gly Thr Gln Lys Phe Lys Ala Ala Ile Asp Gly Asn Gly Phe Lys Gly
                405                 410                 415

Thr Trp Thr Glu Asn Gly Ser Gly Asp Val Ser Gly Lys Phe Tyr Gly
            420                 425                 430

Pro Ala Gly Glu Glu Val Ala Gly Lys Tyr Ser Tyr Arg Pro Thr Asp
            435                 440                 445

Ala Glu Lys Gly Gly Phe Gly Val Phe Ala Gly Lys Lys Glu Gln Asp
            450                 455                 460

<210> SEQ ID NO 7
<211> LENGTH: 644
<212> TYPE: PRT
<213> ORGANISM: Neisseria meningitidis

<400> SEQUENCE: 7

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
        50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240
```

```
Lys Asn Asp Gly Lys Asn Asp Lys Phe Val Gly Leu Val Ala Asp Ser
                245                 250                 255
Val Gln Met Lys Gly Ile Asn Gln Tyr Ile Ile Phe Tyr Lys Pro Lys
            260                 265                 270
Pro Thr Ser Phe Ala Arg Phe Arg Ser Ala Arg Ser Arg Arg Ser
        275                 280                 285
Leu Pro Ala Glu Met Pro Leu Ile Pro Val Asn Gln Ala Asp Thr Leu
        290                 295                 300
Ile Val Asp Gly Glu Ala Val Ser Leu Thr Gly His Ser Gly Asn Ile
305                 310                 315                 320
Phe Ala Pro Glu Gly Asn Tyr Arg Tyr Leu Thr Tyr Gly Ala Glu Lys
                325                 330                 335
Leu Pro Gly Gly Ser Tyr Ala Leu Arg Val Gln Gly Glu Pro Ser Lys
            340                 345                 350
Gly Glu Met Leu Ala Gly Thr Ala Val Tyr Asn Gly Glu Val Leu His
        355                 360                 365
Phe His Thr Glu Asn Gly Arg Pro Ser Pro Ser Arg Gly Arg Phe Ala
        370                 375                 380
Ala Lys Val Asp Phe Gly Ser Lys Ser Val Asp Gly Ile Ile Asp Ser
385                 390                 395                 400
Gly Asp Gly Leu His Met Gly Thr Gln Lys Phe Lys Ala Ala Ile Asp
                405                 410                 415
Gly Asn Gly Phe Lys Gly Thr Trp Thr Glu Asn Gly Gly Asp Val
            420                 425                 430
Ser Gly Lys Phe Tyr Gly Pro Ala Gly Glu Glu Val Ala Gly Lys Tyr
        435                 440                 445
Ser Tyr Arg Pro Thr Asp Ala Glu Lys Gly Gly Phe Gly Val Phe Ala
        450                 455                 460
Gly Lys Lys Glu Gln Asp Gly Ser Gly Gly Gly Ala Thr Tyr Lys
465                 470                 475                 480
Val Asp Glu Tyr His Ala Asn Ala Arg Phe Ala Ile Asp His Phe Asn
                485                 490                 495
Thr Ser Thr Asn Val Gly Gly Phe Tyr Gly Leu Thr Gly Ser Val Glu
            500                 505                 510
Phe Asp Gln Ala Lys Arg Asp Gly Lys Ile Asp Ile Thr Ile Pro Val
        515                 520                 525
Ala Asn Leu Gln Ser Gly Ser Gln His Phe Thr Asp His Leu Lys Ser
        530                 535                 540
Ala Asp Ile Phe Asp Ala Ala Gln Tyr Pro Asp Ile Arg Phe Val Ser
545                 550                 555                 560
Thr Lys Phe Asn Phe Asn Gly Lys Lys Leu Val Ser Val Asp Gly Asn
                565                 570                 575
Leu Thr Met His Gly Lys Thr Ala Pro Val Lys Leu Lys Ala Glu Lys
            580                 585                 590
Phe Asn Cys Tyr Gln Ser Pro Met Ala Lys Thr Glu Val Cys Gly Gly
        595                 600                 605
Asp Phe Ser Thr Thr Ile Asp Arg Thr Lys Trp Gly Val Asp Tyr Leu
        610                 615                 620
Val Asn Val Gly Met Thr Lys Ser Val Arg Ile Asp Ile Gln Ile Glu
625                 630                 635                 640
Ala Ala Lys Gln

<210> SEQ ID NO 8
```

-continued

<211> LENGTH: 434
<212> TYPE: PRT
<213> ORGANISM: Neisseria meningitidis

<400> SEQUENCE: 8

```
Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asn Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
    370                 375                 380

Ala Val Ile Ser Gly Ser Val Leu Tyr Asn Gln Ala Glu Lys Gly Ser
```

```
                385                 390                 395                 400
Tyr Ser Leu Gly Ile Phe Gly Gly Lys Ala Gln Glu Val Ala Gly Ser
                    405                 410                 415

Ala Glu Val Lys Thr Val Asn Gly Ile Arg His Ile Gly Leu Ala Ala
                420                 425                 430

Lys Gln

<210> SEQ ID NO 9
<211> LENGTH: 6
<212> TYPE: PRT
<213> ORGANISM: Neisseria meningitidis

<400> SEQUENCE: 9

Gly Ser Gly Gly Gly Gly
1               5

<210> SEQ ID NO 10
<211> LENGTH: 255
<212> TYPE: PRT
<213> ORGANISM: Neisseria meningitidis

<400> SEQUENCE: 10

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
                180                 185                 190

Leu Ala Ala Ala Asp Ile Lys Pro Asp Gly Lys Arg His Ala Val Ile
            195                 200                 205

Ser Gly Ser Val Leu Tyr Asn Gln Ala Glu Lys Gly Ser Tyr Ser Leu
        210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 11
```

<211> LENGTH: 254
<212> TYPE: PRT
<213> ORGANISM: Neisseria meningitidis

<400> SEQUENCE: 11

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 12
<211> LENGTH: 262
<212> TYPE: PRT
<213> ORGANISM: Neisseria meningitidis

<400> SEQUENCE: 12

```
Cys Ser Ser Gly Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95
```

-continued

```
Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
            115                 120                 125

Asp Ser Leu Ile Asn Gln Arg Ser Phe Leu Val Ser Gly Leu Gly Gly
        130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
                180                 185                 190

Thr Leu Glu Gln Asn Val Glu Leu Ala Ala Ala Glu Leu Lys Ala Asp
            195                 200                 205

Glu Lys Ser His Ala Val Ile Leu Gly Asp Thr Arg Tyr Gly Ser Glu
        210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```